United States Patent
Legisa et al.

(10) Patent No.: US 7,807,404 B2
(45) Date of Patent: Oct. 5, 2010

(54) **MUTATED TRUNCATED MT-*PFK*A GENE FOR THE SYNTHESIS OF ACTIVE SHORTER FRAGMENT OF 6-PHOSPHOFRUCTO-1-KINASE**

(75) Inventors: Matic Legisa, Medvode (SI); Mojca Bencina, Ljubljana (SI); Gregor Tevz, Nazarje (SI); Maja Capuder, Dob pri Domzalah (SI); Tina Mlakar, Radovljica (SI); Darija Oven, Ljubljana (SI)

(73) Assignee: Kemijski Institut, Ljubljana (SI)

( * ) Notice: Subject to any disclaimer, the term of this patent is extended or adjusted under 35 U.S.C. 154(b) by 0 days.

(21) Appl. No.: 12/298,269

(22) PCT Filed: Feb. 27, 2007

(86) PCT No.: PCT/SI2007/000007

§ 371 (c)(1),
(2), (4) Date: Dec. 15, 2008

(87) PCT Pub. No.: WO2007/123498

PCT Pub. Date: Nov. 1, 2007

(65) Prior Publication Data

US 2009/0098605 A1    Apr. 16, 2009

(30) Foreign Application Priority Data

Apr. 26, 2006   (SI) ............................... 200600107

(51) Int. Cl.
*C12N 9/12*    (2006.01)
*C12N 1/00*    (2006.01)
*C07H 21/04*   (2006.01)
*C12P 1/00*    (2006.01)

(52) U.S. Cl. ...................... 435/41; 435/194; 435/252.3; 435/252.33; 435/254.11; 435/254.2; 435/254.3; 435/320.1; 536/23.1; 536/23.2

(58) Field of Classification Search ........................ None
See application file for complete search history.

(56) References Cited

FOREIGN PATENT DOCUMENTS

WO    WO 2005/023854    *   3/2005

OTHER PUBLICATIONS

Eugen Arts, Christian P. Kubicek and Max Röhr, "Regulation of Phosphofructokinase from *Aspergillus niger*: Effect of Fructose 2,6-Biphosphate on the Action of Citrate, Ammonium Ions and AMP," Journal of General Microbiology, copyright 1987, vol. 133, pp. 1195-1199, Great Britain.

Aysen Habison, C.P. Kubicek and M. Röhr, "Phosphofructokinase as a Regulatory Enzyme in Citric Acid Producing *Aspergillus niger*," FEMS Microbiology Letters 5, Federation of European Microbiological Societies, copyright 1979, pp. 39-42, Elsevier/North-Holland Biomedical Press.

Aysen Habison, Christian P. Kubicek and Max Röhr, "Partial purification and regulatory properties of phosphofructokinase from *Aspergillus niger*," Biochemical Journal, copyright 1983, vol. 209, pp. 669-676, Great Britain.

Thomas Hansen, Meike Musfeldt, and Peter Schönheit, "ATP-dependent 6-phosphofructokinase from the hyperthermophilic bacterium *Thermotoga maritima*: characterization of an extremely thermophilic, allosterically regulated enzyme," Arch. Microbiol., copyright 2002, vol. 177, pp. 401-409.

Stephan J. A. Hesse, George J. G. Ruijter, Cor Dijkema, and Jaap Visser, "Intracellular pH homeostasis in the filamentous fungus *Aspergillus niger*," Eur. J. Biochem., copyright 2002, vol. 269, pp. 3485-3494.

Klaus Huse, Bengt Jergil, Wolf-Dieter Schwidop, and Gerhard Kopperschläger, "Evidence for phosphorylation of yeast phosphofructokinase," Elsevier Science Publishers B.V. (Biomedical Division), Federation of European Biochemical Societies, copyright 1988, pp. 185-188.

International Search Report mailed on Oct. 31, 2007 in PCT/SI2007/000007.

Katarina Jernejc and Matic Legiša, "A drop of intracellular pH stimulates citric acid accumulation by some strains of *Aspergillus niger*," Journal of Biotechnology, copyright 2004, vol. 112, pp. 289-297.

Robert G. Kemp and Dhammika Gunasekera, "Evolution of the Allosteric Ligand Sites of Mammalian Phosphofructo-1-kinase," Biochemistry, copyright 2002, vol. 41, No. 30, pp. 9426-9430.

Irwin J. Kurland, M. Raafat El-Maghrabi, John J. Correia, and Simon J. Pilkis, "Rat Liver 6-Phosphofructo-2-kinase/Fructose-2,6-biphosphatase—Properties of Phospho- and Dephospho- Forms and of Two Mutants in Which Ser32 Has Been Changed by Site-Directed Mutagenesis," the Journal of Biological Chemistry, copyright 1992, vol. 267, No. 7, Issue of March 5, pp. 4416-4423, The American Society for Biochemistry and Molecular Biology, Inc.

(Continued)

*Primary Examiner*—Nashaat T Nashed
(74) *Attorney, Agent, or Firm*—Smith Moore Leatherwood LLP

(57) ABSTRACT

The invention deals with mutated truncated mt-pfkA gene encoding shorter fragment of 6-phosphofructo-1-kinase (PFK1), with no need for phosphorylation of the protein molecule for activation, that is not significantly inhibited by citric acid and/or its salts and ATP molecules. Active 49-52 kDa fragment encoded by mt-pfkA gene, retains positive regulatory properties of the native protein and is activated in the presence of specific activators, while citric acid and ATP, important metabolites that function as feed back inhibitors in higher organisms do not reduce its activity. The invention deals with the use of modified shorter fragment in biotechnological processes for fabricating primary and secondary metabolites.

45 Claims, 7 Drawing Sheets

OTHER PUBLICATIONS

I.J. Kurland and S. J. Pilkis, "Covalent control of 6-phosphofructo-2-kinase/fructose-2,6-biphosphatase: Insights into autoregulation of a bifunctional enzyme," Protein Science, copyright 1995, vol. 4, pp. 1023-1037, Cold Spring Harbor Laboratory Press.

Margo A. Kusters-Van Someren, Jan A.M. Harmsen, Harry C.M. Kester, and Jaap Visser, "Structure of the *Aspergillus niger* pelA gene and its expression in *Aspergillus niger* and *Aspergillus nidulans*," Current Genetics, copyright 1991, vol. 20, pp. 293-299, Springer-Verlag.

U.K. Laemmli, "Cleavage of Structural Proteins during the Assembly of the Head of Bacteriophage T4," Nature, copyright 1970, vol. 227, pp. 680-685.

M. Legiša and M. Mattey, "Citrate regulation of the change in carbohydrate degradation during the initial phase of the citric acid production by *Aspergillus niger*," Enzyme Microbial Technology, copyright 1988, vol. 10, pp. 33-36.

Matic Legiša and Mojca Benčina, "Evidence for the activation of 6-phosphofructo-1-kinase by cAMP-dependent protein kinase in *Aspergillus niger*," FEMS Microbiology Letters 118, Federation of European Microbiological Studies, copyright 1994, pp. 327-334.

M. Legiša and M. Benčina, "Evidence for the activation of 6-phosphofructo-1-kinase by cAMP-dependent protein kinase in *Aspergillus niger*," Corrigendum, FEMS Microbiology Letters 118, Federation of European Microbiological Studies, copyright 1994, p. 129.

Yali Li, Diana Rivera, Wei Ru, Dhammika Gunasekera, and Robert G. Kemp, "Identification of Allosteric Sites in Rabbit Phosphofructo-1-kinase," Biochemistry, copyright 1999, vol. 38, No. 49, pp. 16407-16412.

Suzana Mesojednik and Matic Legiša, "Posttranslational Modification of 6-Phosphofructo-1-Kinase in *Aspergillus niger*," Applied and Environmental Microbiology, American Society for Microbiology, copyright Mar. 2005, vol. 71, No. 3, pp. 1425-1432.

Tina Mlakar and Matic Legiša, "Citrate Inhibition-Resistant Form of 6-Phosphofructo-1-Kinase from *Aspergillus niger*," Applied and Environmental Microbiology, American Society for Microbiology, copyright Jul. 2006, pp. 4515-4521.

Roger A. Poorman, Anne Randolph, Robert G. Kemp, and Robert L. Heinrikson, "Evolution of phosphofructokinase gene duplication and creation of new effector sites," Nature, copyright May 1984, vol. 309, pp. 467-469.

Emanuele Riscaldati, Mauro Moresi, Federico Federici, Maurizio Petruccioli, "Effect of pH and stirring rate on itaconate production by *Aspergillus terreus*," Journal of Biotechnology, copyright 2000, vol. 83, pp. 219-230.

G.J.G. Ruijter, H Panneman, and J. Visser, "Overexpression of phosphofructokinase and pyruvate kinase in citric acid-producing *Aspergillus niger*," Biochimica et Biophysica Acta, copyright 1997, vol. 1334, pp. 317-326.

Gerlinde Schreferl, Christian P. Kubicek, and Max Röhr, "Inhibition of Citric Acid Accumulation by Manganese Ions in *Aspergillus niger* Mutants with Reduced Citrate Control of Phosphofructokinase," Journal of Bacteriology, American Society for Microbiology, copyright Mar. 1986, pp. 1019-1022.

Algimantas P. Valaitis, Lawrence G. Foe, and Robert G. Kemp, "Desensitization of Muscle Phosphofructokinase to ATP Inhibition by Removal of a Carboxyl-terminal Heptadecapeptide," The Journal of Biological Chemistry, copyright 1987, vol. 262, No. 11, pp. 5044-5048.

Wolf Vishniac and Melvin Santer, "The Thiobacilli," Department of Microbiology, pp. 195-213, Yale University, New Haven, Connecticut.

Xiaojun Wang and Robert G. Kemp, "Reaction Path of Phosphofructo-1-kinase Is Altered by Mutagenesis and Alternative Substrates," Biochemistry, copyright 2001, vol. 40, No. 13, pp. 3938-3942.

Written Opinion mailed on Oct. 31, 2007 in PCT/SI2007/000007.

* cited by examiner

SEQUENCE LISTING

```
<160> NUMBER OF SEQ ID NOS: 20

<210> SEQ ID NO 1
<211> LENGTH: 452
<212> TYPE: PRT
<213> ORGANISM: Aspergillus niger

<400> SEQUENCE: 1

Met Ala Pro Pro Gln Ala Pro Val Gln Pro Lys Arg Arg Arg Ile
1               5                   10                  15

Gly Val Leu Thr Ser Gly Gly Asp Ala Pro Gly Met Asn Gly Val Val
            20                  25                  30

Arg Ala Val Val Arg Met Ala Ile His Ser Asp Cys Glu Ala Phe Ala
        35                  40                  45

Val Tyr Glu Gly Tyr Glu Gly Leu Val Asn Gly Gly Asp Met Ile Arg
    50                  55                  60

Gln Leu His Trp Glu Asp Val Arg Gly Trp Leu Ser Arg Gly Gly Thr
65                  70                  75                  80

Leu Ile Gly Ser Ala Arg Cys Met Glu Phe Arg Glu Arg Pro Ile Arg
                85                  90                  95

Leu Arg Ala Ala Lys Asn Met Val Leu Arg Gly Ile Asp Ala Leu Val
                100                 105                 110
```

```
Val Cys Gly Gly Asp Gly Ser Leu Thr Gly Ala Asp Val Phe Arg Ser
        115                 120                 125

Glu Trp Pro Gly Leu Leu Lys Glu Leu Val Glu Thr Gly Glu Leu Thr
        130                 135                 140

Glu Glu Gln Val Lys Pro Tyr Gln Ile Leu Asn Ile Val Gly Leu Val
145                 150                 155                 160

Gly Ser Ile Asp Asn Asp Met Ser Gly Thr Asp Ala Thr Ile Gly Cys
                165                 170                 175

Tyr Ser Ser Leu Thr Arg Ile Cys Asp Ala Val Asp Asp Val Phe Asp
                180                 185                 190

Thr Ala Phe Ser His Gln Arg Gly Phe Val Ile Glu Val Met Gly Arg
        195                 200                 205

His Cys Gly Trp Leu Ala Leu Met Ser Ala Ile Ser Thr Gly Ala Asp
        210                 215                 220

Trp Leu Phe Val Pro Glu Met Pro Pro Lys Asp Gly Trp Glu Asp Asp
225                 230                 235                 240

Met Cys Ala Ile Ile Thr Lys Asn Arg Lys Glu Arg Gly Lys Arg Arg
                245                 250                 255

Thr Ile Val Ile Val Ala Glu Gly Ala Gln Asp Arg His Leu Asn Lys
                260                 265                 270

Ile Ser Ser Ser Lys Ile Lys Asp Ile Leu Thr Glu Arg Leu Asn Leu
        275                 280                 285

Asp Thr Arg Val Thr Val Leu Gly His Thr Gln Arg Gly Gly Ala Ala
        290                 295                 300

Cys Ala Tyr Asp Arg Trp Leu Ser Thr Leu Gln Gly Val Glu Ala Val
305                 310                 315                 320

Arg Ala Val Leu Asp Met Lys Pro Glu Ala Pro Ser Pro Val Ile Thr
                325                 330                 335

Ile Arg Glu Asn Lys Ile Leu Arg Met Pro Leu Met Asp Ala Val Gln
        340                 345                 350

His Thr Lys Thr Val Thr Lys His Ile Gln Asn Lys Glu Phe Ala Glu
        355                 360                 365

Ala Met Ala Leu Arg Asp Ser Glu Phe Lys Glu Tyr His Phe Ser Tyr
370                 375                 380

Ile Asn Thr Ser Thr Pro Asp His Pro Lys Leu Leu Leu Pro Glu Asn
385                 390                 395                 400

Lys Arg Met Arg Ile Gly Ile Ile His Val Gly Ala Pro Ala Gly Gly
                405                 410                 415

Met Asn Gln Ala Thr Arg Ala Ala Val Ala Tyr Cys Leu Thr Arg Gly
                420                 425                 430

His Thr Pro Leu Ala Ile His Asn Gly Phe Pro Gly Leu Cys Arg His
        435                 440                 445

Tyr Asp Pro Gly
        450

<210> SEQ ID NO 2
<211> LENGTH: 452
<212> TYPE: PRT
<213> ORGANISM: Aspergillus niger

<400> SEQUENCE: 2

Met Ala Pro Pro Gln Ala Pro Val Gln Pro Pro Lys Arg Arg Arg Ile
1               5                   10                  15

Gly Val Leu Thr Ser Gly Gly Asp Ala Pro Gly Met Asn Gly Val Val
```

```
                    20                  25                  30
Arg Ala Val Val Arg Met Ala Ile His Ser Asp Cys Glu Ala Phe Ala
            35                  40                  45
Val Tyr Glu Gly Tyr Glu Gly Leu Val Asn Gly Gly Asp Met Ile Arg
        50                  55                  60
Gln Leu His Trp Glu Asp Val Arg Gly Trp Leu Ser Arg Gly Gly Thr
65                  70                  75                  80
Leu Ile Gly Ser Ala Arg Cys Met Glu Phe Arg Glu Arg Pro Gly Arg
                85                  90                  95
Leu Arg Ala Ala Lys Asn Met Val Leu Arg Gly Ile Asp Ala Leu Val
            100                 105                 110
Val Cys Gly Gly Asp Gly Ser Leu Thr Gly Ala Asp Val Phe Arg Ser
        115                 120                 125
Glu Trp Pro Gly Leu Leu Lys Glu Leu Val Glu Thr Gly Glu Leu Thr
        130                 135                 140
Glu Glu Gln Val Lys Pro Tyr Gln Ile Leu Asn Ile Val Gly Leu Val
145                 150                 155                 160
Gly Ser Ile Asp Asn Asp Met Ser Gly Thr Asp Ala Thr Ile Gly Cys
                165                 170                 175
Tyr Ser Ser Leu Thr Arg Ile Cys Asp Ala Val Asp Asp Val Phe Asp
            180                 185                 190
Thr Ala Phe Ser His Gln Arg Gly Phe Val Ile Glu Val Met Gly Arg
        195                 200                 205
His Cys Gly Trp Leu Ala Leu Met Ser Ala Ile Ser Thr Gly Ala Asp
    210                 215                 220
Trp Leu Phe Val Pro Glu Met Pro Pro Lys Asp Gly Trp Glu Asp Asp
225                 230                 235                 240
Met Cys Ala Ile Ile Thr Lys Asn Arg Lys Glu Arg Gly Lys Arg Arg
                245                 250                 255
Thr Ile Val Ile Val Ala Glu Gly Ala Gln Asp Arg His Leu Asn Lys
            260                 265                 270
Ile Ser Ser Ser Lys Ile Lys Asp Ile Leu Thr Glu Arg Leu Asn Leu
        275                 280                 285
Asp Thr Arg Val Thr Val Leu Gly His Thr Gln Arg Gly Gly Ala Ala
    290                 295                 300
Cys Ala Tyr Asp Arg Trp Leu Ser Thr Leu Gln Gly Val Glu Ala Val
305                 310                 315                 320
Arg Ala Val Leu Asp Met Lys Pro Glu Ala Pro Ser Pro Val Ile Thr
                325                 330                 335
Ile Arg Glu Asn Lys Ile Leu Arg Met Pro Leu Met Asp Ala Val Gln
            340                 345                 350
His Thr Lys Thr Val Thr Lys His Ile Gln Asn Lys Glu Phe Ala Glu
        355                 360                 365
Ala Met Ala Leu Arg Asp Ser Glu Phe Lys Glu Tyr His Phe Ser Tyr
    370                 375                 380
Ile Asn Thr Ser Thr Pro Asp His Pro Lys Leu Leu Leu Pro Glu Asn
385                 390                 395                 400
Lys Arg Met Arg Ile Gly Ile Ile His Val Gly Ala Pro Ala Gly Gly
                405                 410                 415
Met Asn Gln Ala Thr Arg Ala Ala Val Ala Tyr Cys Leu Thr Arg Gly
            420                 425                 430
His Thr Pro Leu Ala Ile His Asn Gly Phe Pro Gly Leu Cys Arg His
        435                 440                 445
```

Tyr Asp Pro Gly
    450

<210> SEQ ID NO 3
<211> LENGTH: 785
<212> TYPE: PRT
<213> ORGANISM: Aspergillus niger

<400> SEQUENCE: 3

Met Ala Pro Pro Gln Ala Pro Val Gln Pro Lys Arg Arg Ile
 1               5                  10                  15

Gly Val Leu Thr Ser Gly Gly Asp Ala Pro Gly Met Asn Gly Val Val
                20                  25                  30

Arg Ala Val Val Arg Met Ala Ile His Ser Asp Cys Glu Ala Phe Ala
            35                  40                  45

Val Tyr Glu Gly Tyr Glu Gly Leu Val Asn Gly Gly Asp Met Ile Arg
        50                  55                  60

Gln Leu His Trp Glu Asp Val Arg Gly Trp Leu Ser Arg Gly Gly Thr
65                  70                  75                  80

Leu Ile Gly Ser Ala Arg Cys Met Thr Phe Arg Glu Arg Pro Gly Arg
                85                  90                  95

Leu Arg Ala Ala Lys Asn Met Val Leu Arg Gly Ile Asp Ala Leu Val
            100                 105                 110

Val Cys Gly Gly Asp Gly Ser Leu Thr Gly Ala Asp Val Phe Arg Ser
        115                 120                 125

Glu Trp Pro Gly Leu Leu Lys Glu Leu Val Glu Thr Gly Glu Leu Thr
    130                 135                 140

Glu Glu Gln Val Lys Pro Tyr Gln Ile Leu Asn Ile Val Gly Leu Val
145                 150                 155                 160

Gly Ser Ile Asp Asn Asp Met Ser Gly Thr Asp Ala Thr Ile Gly Cys
                165                 170                 175

Tyr Ser Ser Leu Thr Arg Ile Cys Asp Ala Val Asp Asp Val Phe Asp
            180                 185                 190

Thr Ala Phe Ser His Gln Arg Gly Phe Val Ile Glu Val Met Gly Arg
        195                 200                 205

His Cys Gly Trp Leu Ala Leu Met Ser Ala Ile Ser Thr Gly Ala Asp
    210                 215                 220

Trp Leu Phe Val Pro Glu Met Pro Pro Lys Asp Gly Trp Glu Asp Asp
225                 230                 235                 240

Met Cys Ala Ile Ile Thr Lys Asn Arg Lys Glu Arg Gly Lys Arg Arg
                245                 250                 255

Thr Ile Val Ile Val Ala Glu Gly Ala Gln Asp Arg His Leu Asn Lys
            260                 265                 270

Ile Ser Ser Ser Lys Ile Lys Asp Ile Leu Thr Glu Arg Leu Asn Leu
        275                 280                 285

Asp Thr Arg Val Thr Val Leu Gly His Thr Gln Arg Gly Gly Ala Ala
    290                 295                 300

Cys Ala Tyr Asp Arg Trp Leu Ser Thr Leu Gln Gly Val Glu Ala Val
305                 310                 315                 320

Arg Ala Val Leu Asp Met Lys Pro Glu Ala Pro Ser Pro Val Ile Thr
                325                 330                 335

Ile Arg Glu Asn Lys Ile Leu Arg Met Pro Leu Met Asp Ala Val Gln
            340                 345                 350

His Thr Lys Thr Val Thr Lys His Ile Gln Asn Lys Glu Phe Ala Glu

-continued

```
                355                 360                 365
Ala Met Ala Leu Arg Asp Ser Glu Phe Lys Glu Tyr His Phe Ser Tyr
    370                 375                 380
Ile Asn Thr Ser Thr Pro Asp His Pro Lys Leu Leu Leu Pro Glu Asn
385                 390                 395                 400
Lys Arg Met Arg Ile Gly Ile His Val Gly Ala Pro Ala Gly Gly
                405                 410                 415
Met Asn Gln Ala Thr Arg Ala Ala Val Ala Tyr Cys Leu Thr Arg Gly
            420                 425                 430
His Thr Pro Leu Ala Ile His Asn Gly Phe Pro Gly Leu Cys Arg His
        435                 440                 445
Tyr Asp Asp Thr Pro Ile Cys Ser Val Arg Glu Val Ala Trp Gln Glu
    450                 455                 460
Ser Asp Ala Trp Val Asn Glu Gly Gly Ser Asp Ile Gly Thr Asn Arg
465                 470                 475                 480
Gly Leu Pro Gly Asp Asp Leu Ala Thr Thr Ala Lys Ser Phe Lys Lys
                485                 490                 495
Phe Gly Phe Asp Ala Leu Phe Val Val Gly Gly Phe Glu Ala Phe Thr
            500                 505                 510
Ala Val Ser Gln Leu Arg Gln Ala Arg Glu Lys Tyr Pro Glu Phe Lys
        515                 520                 525
Ile Pro Met Thr Val Leu Pro Ala Thr Ile Ser Asn Asn Val Pro Gly
    530                 535                 540
Thr Glu Tyr Ser Leu Gly Ser Asp Thr Cys Leu Asn Thr Leu Ile Asp
545                 550                 555                 560
Phe Cys Asp Ala Ile Arg Gln Ser Ala Ser Ser Arg Arg Arg Val
                565                 570                 575
Phe Val Ile Glu Thr Gln Gly Gly Lys Ser Gly Tyr Ile Ala Thr Thr
            580                 585                 590
Ala Gly Leu Ser Val Gly Ala Val Ala Val Tyr Ile Pro Glu Glu Gly
        595                 600                 605
Ile Asp Ile Lys Met Leu Ala Arg Asp Ile Asp Phe Leu Arg Asp Asn
    610                 615                 620
Phe Ala Arg Asp Lys Gly Ala Asn Arg Ala Gly Lys Ile Ile Leu Arg
625                 630                 635                 640
Asn Glu Cys Ala Ser Ser Thr Tyr Thr Thr Gln Val Val Ala Asp Met
                645                 650                 655
Ile Lys Glu Glu Ala Lys Gly Arg Phe Glu Ser Arg Ala Ala Val Pro
            660                 665                 670
Gly His Phe Gln Gln Gly Gly Lys Pro Ser Pro Met Asp Arg Ile Arg
        675                 680                 685
Ala Leu Arg Met Ala Thr Lys Cys Met Leu His Leu Glu Ser Tyr Ala
    690                 695                 700
Gly Lys Ser Ala Asp Glu Ile Ala Ala Asp Glu Leu Ser Ala Ser Val
705                 710                 715                 720
Ile Gly Ile Lys Gly Ser Gln Val Leu Phe Ser Pro Met Gly Gly Glu
                725                 730                 735
Thr Gly Leu Glu Ala Thr Glu Thr Asp Trp Ala Arg Arg Pro Lys
            740                 745                 750
Thr Glu Phe Trp Leu Glu Leu Gln Asp Thr Val Asn Ile Leu Ser Gly
        755                 760                 765
Arg Ala Ser Val Asn Asn Ala Thr Trp Ser Cys Tyr Glu Asn Ala Pro
    770                 775                 780
```

Gly
785

<210> SEQ ID NO 4
<211> LENGTH: 2461
<212> TYPE: DNA
<213> ORGANISM: Aspergillus niger

<400> SEQUENCE: 4

| | | | | | |
|---|---|---|---|---|---|
| atggctcccc | cccaagctcc | cgtgcaaccg | cccaagagac | gccgcatcgg | tgtcttgacc | 60 |
| tctggtggcg | atgctcccgg | tatgaacggt | gtcgtccggg | ccgtcgtccg | gatggctatc | 120 |
| cactccgact | gtgaggcttt | cgccgtctac | gaaggttacg | agggtctcgt | caatggcggc | 180 |
| gacatgatcc | gtcagcttca | ctgggaggat | gttcgcggct | ggttgtcccg | tggtggtacc | 240 |
| ttgatcggtt | ccgcccgctg | catgaccttc | cgtgagcgcc | ccggtcgtct | gcgggctgcc | 300 |
| aagaacatgg | tcctccgtgg | cattgacgcc | ttgtcgtct | gtggtggtga | tggcagtttg | 360 |
| actggtgccg | acgtttttcg | ttccgagtgg | cccggtctgt | tgaaggaatt | ggtcgagacg | 420 |
| ggcgagttga | ccgaagagca | ggtcaagcca | taccagattc | tgaacatcgt | cggtttggtg | 480 |
| ggttcgatcg | ataacgacat | gtccggcacc | gacgccacca | tcggttgcta | ctcctcccct | 540 |
| actcgcatct | gtgacgccgt | cgacgacgtc | ttcgatactg | ccttttccca | ccagcgtgga | 600 |
| ttcgtcattg | aggtcatggg | tcgtcactgc | ggttggctgg | ccttgatgtc | tgctatcagt | 660 |
| accggtgccg | actggctgtt | cgtgcccgag | atgccgccca | aggacggatg | ggaggatgac | 720 |
| atgtgcgcta | tcattaccaa | ggtgggttga | tcggaacttg | gtggagagaa | ctcagaggca | 780 |
| tcactaactc | cccgcagaac | agaaaggagc | gtggaaagcg | taggacgatc | gtcatcgtgg | 840 |
| ccgagggtgc | ccaggatcgc | catctcaaca | agatctcgag | ttcgaagatc | aaggatattt | 900 |
| tgacggagcg | gttgaacctg | gatacccgtg | tgactgtgtt | gggtcacact | cagagaggtg | 960 |
| gagccgcctg | tgcgtacgac | cgctggctgt | ccacactgca | gggtgtcgag | gctgtccgcg | 1020 |
| cggtgctgga | catgaagccc | gaagcccgt | ccccggtcat | caccatccgt | gagaacaaga | 1080 |
| tcttgcgcat | gccgttgatg | gacgccgtgc | agcacaccaa | gactgtcacc | aagcacattc | 1140 |
| agaacaagga | gttcgccgaa | gccatggccc | tccgcgactc | ggaattcaaa | gagtaccact | 1200 |
| tttcctacat | caacacttcc | acgcccgacc | acccgaagct | gctcctccca | gagaacaagg | 1260 |
| tttgtcgcca | cagtagctgc | ttcggtgctg | agctaacaaa | aggcagagaa | tgcgcatcgg | 1320 |
| tattattcac | gttggcgccc | ccgctggtgg | tatgaaccag | gctacccgcg | cggccgttgc | 1380 |
| ctactgcctg | actcgtggcc | acaccccct | ggccattcac | aacggtttcc | ccggtctgtg | 1440 |
| ccggcactat | gatgacaccc | cgatctgctc | tgtgcgcgag | gtggcatggc | aggaatcgga | 1500 |
| cgcctgggtc | aacgagggtg | gttcggatat | cggtaccaac | cgtggtctgc | ccggcgatga | 1560 |
| cctcgcgacc | acgcgaaga | gcttcaagaa | gttcggattc | gatgcgttgt | tcgtcgtggg | 1620 |
| tggatttgag | gcgttcaccg | ccgtcagcca | gcttcgccag | gcgcgcgaga | agtaccccga | 1680 |
| attcaagatt | cccatgaccg | tgctgccggc | gaccatttcc | aacaacgtgc | cgggcacaga | 1740 |
| atactctctg | ggtagcgaca | cctgccttaa | caccttgatc | gacttctgcg | acgccatccg | 1800 |
| ccagtcggcc | tcgtcctctc | gtcgccgtgt | gttcgtcatc | gagacgcagg | gtggcaagtc | 1860 |
| gggttacatc | gccacgacgg | ctggtctgtc | ggtgggcgcg | gtagccgtgt | acattcccga | 1920 |
| ggagggcatc | gacattaaga | tgctggcccg | cgacattgac | ttcctgcgtg | caactttgc | 1980 |
| gcgcgacaag | ggagcgaacc | gcgccggtaa | gatcatcctg | cgtaacgagt | gcgcgtccag | 2040 |

-continued

```
cacgtacacg acacaggtgg tggccgacat gatcaaggag gaagccaagg gacgtttcga    2100
gagtcgtgcg gcggtgccgg gacacttcca gcagggtggc aagccgtcgc cgatggaccg    2160
tatccgggcg ttgcggatgg ccaccaagtg tatgctgcac ctggagagct atgcgggcaa    2220
gtcggcggat gagattgcgg ccgatgagct gtctgcgtcg gtcattggta tcaagggctc    2280
gcaggtgttg ttctcgccga tgggtggaga gaccggcctg gaggcgaccg agacggactg    2340
ggcgcgccgt cgacccaaga cggagttctg gctggagctg caggacacgg tgaacattct    2400
gtcgggacgg gcgagcgtga acaacgcgac gtggagttgc tatgagaatg ctcccgggta    2460
a                                                                    2461
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gagctcgtga ccggtgactc tttc                                            24

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tctagatgca tatgggtgat gtctgctcaa gc                                   32

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ccatgggtct agacggatcc tagtgattta atagctccat gtc                       43

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gaattcaagc ttccgcggcc gggtattggg tg                                   32

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ccgcggatgc atatggctcc cccccaagc                                    29

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggatcctta cccgggatca tagtgccggc acagacc                           37

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgcccgctg catggagttc cgtgagcgcc c                                 31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggcgctcac ggaactccat gcagcgggcg g                                 31

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgctgcatg gagttccgtg agcgccccat ccgtctgcgg g                      41

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccgcagacg gatgggcgc tcacggaact ccatgcagcg g                       41

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

-continued ccatcgcacg catatggctc c                                             21

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgttctcgt cacggaactc ggggaagcgg gcggaaccga tcaag                   45

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccgagttcc gtgacgagaa catccgtctg cgggctgcc                          39

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taggcgttta tcgctgcttc tagaggatcc ttacccggga tcatag                  46

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccatcgcacg catatggctc c                                             21

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
taggcgttta tcgctgcttc tagaggatcc ttacccggga tcatag                  46

MUTATED TRUNCATED MT-*PFKA* GENE FOR THE SYNTHESIS OF ACTIVE SHORTER FRAGMENT OF 6-PHOSPHOFRUCTO-1-KINASE

This application is a national stage application under 35 U.S.C. 371 of international application no. PCT/SI2007/000007 filed 27 Feb. 2007, and claims priority to Slovenian Application No. P-200600107 filed 26 Apr. 2006, the disclosures of which are expressly incorporated herein by reference.

The subject of the invention is mutated truncated mt-pfkA gene encoding the synthesis of an active shorter fragment of 6-phosphofructo-1-kinase (PFK1), with no posttranslational modification needed to induce the activity. The subject of the invention is the use of mutated truncated gene and its protein product for enhancing the rate of cell biomass synthesis and excretion of extracellular enzymes, as well as increasing the productivity of primary and secondary metabolites.

The invention is in the field of microbial biotechnology and biochemistry.

At biotechnological processes a crucial determinant for the final price of the product is the velocity of the product formation. By optimising the processes the final goal is to change micro-organisms, as well as growth conditions to get higher amounts of substrate transformed into the final product per time unit.

In commercial micro-organisms that are capable of excreting specific biotechnological products with increased productivity and yield, anaplerotic reactions are of crucial importance. Such reactions lead to increased concentrations of tricarboxylic cycle (TCA) intermediates in the cells, which are precursors for a number of biosynthetic pathways, since TCA cycle presents the crucial link between catabolic and anabolic reactions in the cells. By increasing the level of TCA cycle intermediates due to increased anaplerotic reactions, the synthesis of the key cellular building blocks, such as lipids, amino acids, porfirins etc. is enhanced, and consequently the rate of synthesis of primary and secondary metabolites of biotechnological value increased.

Several specific metabolic reactions belong to anaplerotic reactions, however uninterrupted metabolic flow through glycolysis seems to be of utmost importance. The enzyme with the key role in regulating glycolysis is 6-phosphofructo-1-kinase (PFK1). In eukaryotic organisms the enzyme is regulated by the feed back mechanism, by citrate and ATP inhibition. In other words its activity decreases when citric acid level, as an important intermediate of TCA cycle and ATP, as the final product of oxidative phosphorylation, increase over a certain level (Voet and Voet, 1995). In fact negative regulation of the enzyme activity diminishes the effectiveness of anapletoric reactions and consequently reduces the rate of synthesis of the final products. A significant increase in the rate of product formation could be achieved by having undisturbed metabolic flow through glycolysis, which could be done by inserting a modified gene encoding PFK1 enzyme that would be resistant to citrate inhibition but sensitive to activation with specific effectors.

In past several attempts were described to increase metabolic flow through glycolysis with the final goal to stimulate the synthesis of the final products, however no success was recorded. In order to enhance the glycolysis, three genes coding for the key regulatory enzymes of the pathway were isolated from the fungus *Aspergillus niger* including the pfkA gene coding for 6-phosphofructo-1-kinase. The genes were re-introduced into *A. niger* strain in a higher copy number with the ultimate goal to increase the concentration of the key enzymes and increase the flow of metabolites through the glycolysis. However, the detailed analyses of the transformants have not confirmed the expected results. It was concluded that other complex regulatory mechanisms compensated increased concentration of the key enzymes (Ruijter et al., 1996). In another attempt to improve the properties of PFK1, *Aspergillus niger* cells were subjected to mutations in order to make the enzyme resistant to citrate inhibition. A mutant was isolated that showed reduced inhibition by citrate, however the enzyme retained only 20% of its maximal velocity when inhibitor was present at slightly increased concentration of 10 mM. A partially increased resistance toward the citrate inhibition had no positive effect on elevating the rate of product formation (Schreferl et al., 1986). In another attempt reduced inhibition by citrate of PFK1 was obtained by cleaving 8 amino acid residues from the C-terminal part of the enzyme, isolated from the rabbit muscle. Modified enzyme has lost its activity only when 10 mM of citrate was present in the system, while the original enzyme was completely inactivated at 2.5 mM of inhibitor (Valaitis et al., 1987).

The PFK1 isolated from *Aspergillus niger* cells showed more resistance toward the citrate inhibition in comparison to the enzymes from other organisms, yet 10 mM of citrate almost prevented its catalytic activity. Physiological concentration of citric acid in normal cells is in mM values, however in *A. niger* cells the citrate concentration can reach up to 10 mM (Legiša and Kidrič, 1989). PFK1 enzyme isolated from the fungus *Aspergillus niger* was in past often a subject of investigation (Habison et al., 1979; Habison et al., 1983; Schreferel et al. 1986; Arst et al., 1987), moreover a gene coding for PFK1 has been cloned and sequenced. By analyzing the pfkA gene (EMBL accession number pfkA Z79690) it could be concluded that the protein has a molecular mass of 85 kDa, while by studying enzyme kinetics on a partially purified protein, whose molecular weight was not determined, confirmed that AMP, fructose-2,6-bisphosphate and ammonium ions act as positive effectors (Habison et al., 1983). It was also suggested the ammonium ions decrease the inhibition of PFK1 by citrate to a certain extent (Habison et al., 1983; Arst et al., 1987). In authors lab a shorter form of PFK1 isolated from the *Aspergillus niger* was described with molecular mass of about 48 kDa, which initially showed no activity, but became active after phopshorylation of the protein molecule. (Legiša and Benčina, 1994a). C. P. Kubicek, who led investigations of kinetic measurements on the enzyme isolated from *A. niger* (Habison et al., 1979; Habison et al., 1983; Schreferel et al. 1986; Arst et al., 1987) categorically denied that in his lab a protein of 48 kDa showing the PFK1 activity was ever measured (Legiša and Benčina, 1994b). In two diploma projects conducted in authors' labs, the procedure for isolation of 48 kDa fragment was described (Smerkolj, 2000) and post-translational modification of the native protein proposed as a mechanism of fragmented enzyme formation (Mesojednik, 2003). Recently the molecular weight of the active shorter fragment was determined to be 49 kDa, as well as post-translational modification and kinetic parameters of the shorter fragment were described (Mesojednik and Legiša, 2005). By an in vitro experiment it has been shown, that the shorter fragment was inactive immediately after the proteolytic cleavage of the native protein and regained its activity only after the phosphorylation of the protein molecule, mediated by cAMP-dependent protein kinase. Measurements of kinetic parameters revealed that the shorter fragment was resistant to citrate inhibition (Mlakar, diploma work), while the negative effect of ATP was suppressed in the presence of fructose-2,6-bisphosphate (Mesojednik and Legiša, 2005). In literature there is no description of any eukaryotic post-translationally modified PFK1 enzyme with retained ability to be up regulated by specific effectors and lost negative regulation. It seems that the shorter fragment of PFK1 enzyme from *A. niger* cells is the most efficient form of PFK1 enzyme described so far.

In order to avoid complicated posttranslational modification, the shorter PFK1 fragment was prepared from a truncated pfkA gene. A number of genes shortened at 3' end of the leading strain were prepared and transferred into *A. niger* cells. After induced phosphorylation, PFK1 activity characteristic for the shorter fragment was detected in homogenate of transformants carrying t-pfkA gene of specific length (Capuder, 2004). Intracellular phosphorylation was induced by the addition of sodium azide, a well known inhibitor of electron transport at cytochrome oxidase $aa_3$ site, which interrupts the synthesis of ATP which decreases the activity of trans-membrane proton pumps ($H^+$-ATPases). Protons that accumulate in cells cause a decrease in intracellular pH value. It is well known that a drop of intracellular pH triggers cAMP synthesis in fungal cells, which induces the activity of cAMP-dependent protein kinase that finally phosphorylates and activates the shorter fragment of PFK1 enzyme.

Although the shorter fragment might be synthesised in vivo from a truncated gene, the enzyme is initially inactive. It is activated only after the phosphorylation of the protein molecule by cAMP-dependent protein kinase that is induced by an increase of cAMP level in the cells. During *Aspergillus niger* growth cyclic AMP is synthesised after specific changes that spontaneously appear in the medium or it might be triggered artificially by adding specific inhibitors, like azide, to the medium. According to our knowledge spontaneous drop of intracellular pH occurs only in one strain of *A. niger* (A60), where the shorter fragment could be spontaneously activated as well. In another *A. niger* strain (A158) more powerful $H^+$-ATPases are present that prevent intracellular acidification and also synthesis of cAMP (Jernejc and Legiša, 2004). In some micro-organisms mechanisms are known, that trigger cAMP formation and activation of kinases that might activate the shorter fragment of PFK1, however such environmental conditions are often contradictory to optimal conditions needed for the synthesis of biotechnological products.

By introducing specific mutations into the truncated t-pfkA gene, the need for phosphorylation of the protein molecule would be omitted.

By literature search some papers were found that describe changed kinetic parameters of PFK1 enzyme after induced changes in nucleotide sequences. However, in those publications authors used site-directed mutagenesis for determination of allosteric binding sites for various effectors. For example a paper of Li et al., 1999, summarises studies of citrate binding sites that were determined on rabbit muscle PFK1 enzyme, while in review paper of Kemp and Gunasekera, 2002 the evolution of allosteric sites on eukaryotic PFK1 enzymes is presented. No mutations were introduced to change phosphorylation sites on PFK1 enzyme so far. Regulation of the enzyme activity was studied more in detail on 6-phosphofructo-2-kinase/fructose-2,6-bisphosphatase (Kurland et al., 1992; Kurland and Pilkis, 1995), however this enzyme is not directly involved in glycolysis.

No patent could be found that would protect the use of PFK1 enzyme with changed kinetic parameters, by the active form of enzyme synthesised only from a mutated gene.

According to the state-of-art, the problem of the synthesis of an active shorter fragment of PFK1 with improved enzyme characteristics is not sufficiently solved. The aim of the invention is to solve the problem by the procedure that eliminates the need for phosphorylation of the protein molecule for its activation and enables in vivo synthesis of an active protein by inserting modified mt-pfkA gene.

De-regulated glycolytic flux is of utmost importance in commercial micro-organisms for achieving high rates of specific productivity. Such conditions can be accomplished by inserting mutated, truncated mt-pfkA gene, encoding active shorter fragment of PFK1 enzyme that is resistant to citrate inhibition, while other effectors increase its activity to a greater extent in respect to the native enzyme.

According to the invention the task is solved according to independent patent claims.

The present invention addresses the mutated gene, encoding active shorter fragment of 6-phosphofructo-1-kinase, where phosphorylation of the protein molecule is not needed for its activation, whose monomeric molecular mass is between 30 and 55 kDa; whose enzyme activity is not significantly inhibited by citric acid or citrate salts or ATP. The present invention concentrates on the mutated gene encoding shorter fragment of PFK1 that is active immediately after its synthesis and is not inhibited by citric acid, or citrate salts in the range from 0 mM to 10 mM or ATP up to 1.5 ATP in the presence of fructose-2,6-bisphosphate. The invention addresses the modified gene encoding the synthesis of active shorter fragment of PFK1 that can be activated by some metabolites such as fructose-2,6-bisphosphate, ammonium ions and AMP. The shorter fragment originates from the native enzyme with removed N- and/or C-terminal.

The present invention is based on observation that mutated truncated gene, encoding the active fragment of 6-phosphofructo-1-kinase that is resistant to the inhibition by citric acid and/or citrate salts and ATP, increases the rate of primary and secondary metabolite synthesis in the cells.

The invention concentrates on a procedure that includes the use of the mutated gene for the synthesis of the active shorter PFK1 fragment, or insertion of homologous or heterologous gene into the cells for increasing the rate of primary and secondary metabolite synthesis due to increased glycolytic flux.

DESCRIPTION OF FIGURES

FIG. 3a: transformants originating from A645 strain (derivative of A158 strain). FIG. 3b: transformants originating from A60 strain.

DEFINITIONS

Figure 1:
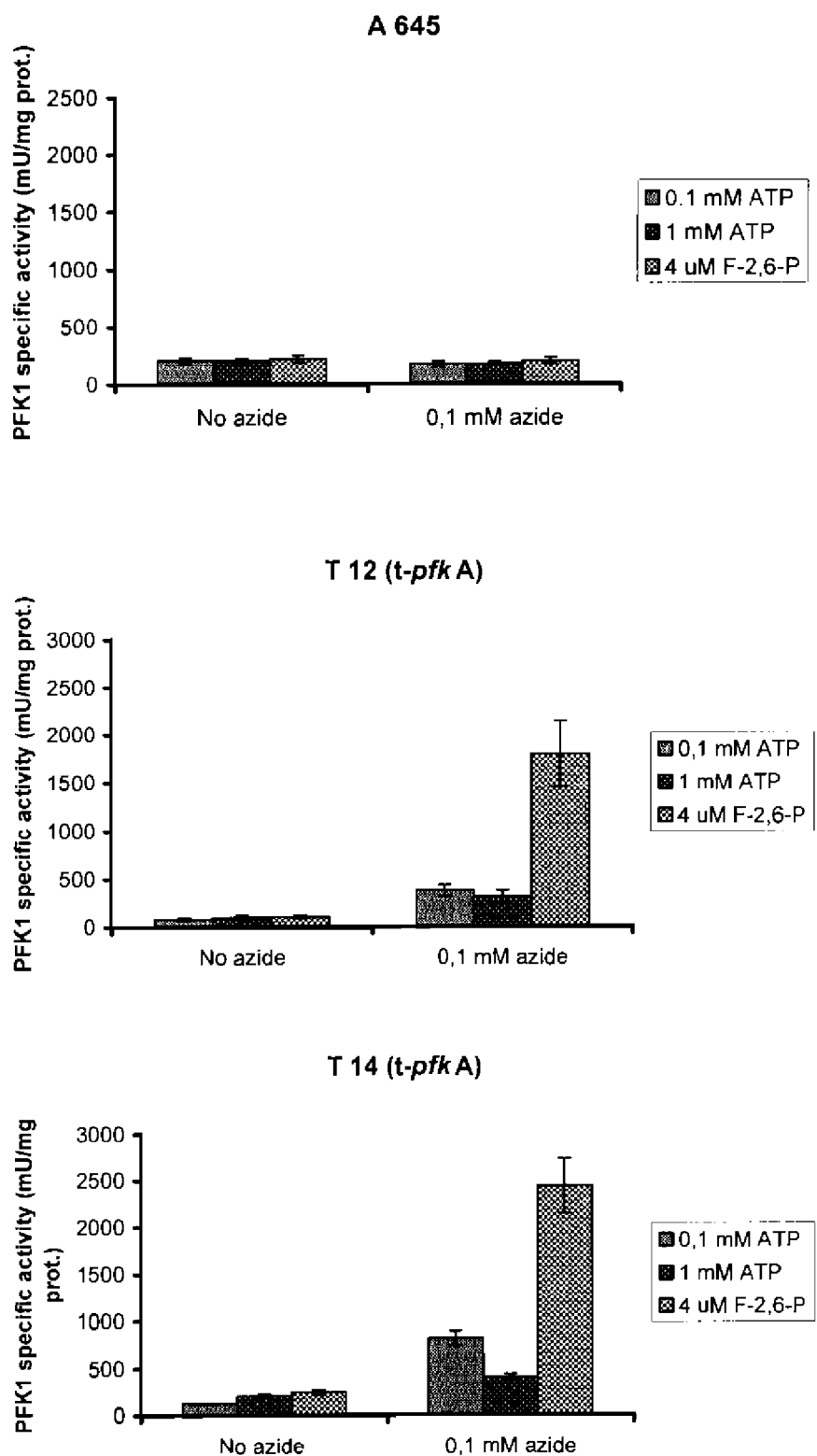
FIG. 1: Specific activities of PFK1 enzymes measured in homogenates of parental strain of *Aspergillus niger* (A645, which is a derivative of A158 strain) and two transformants (T12 and T14) with integrated t-pfkA gene, before and after the induction of phosphorylation by azide.
Figure 2:
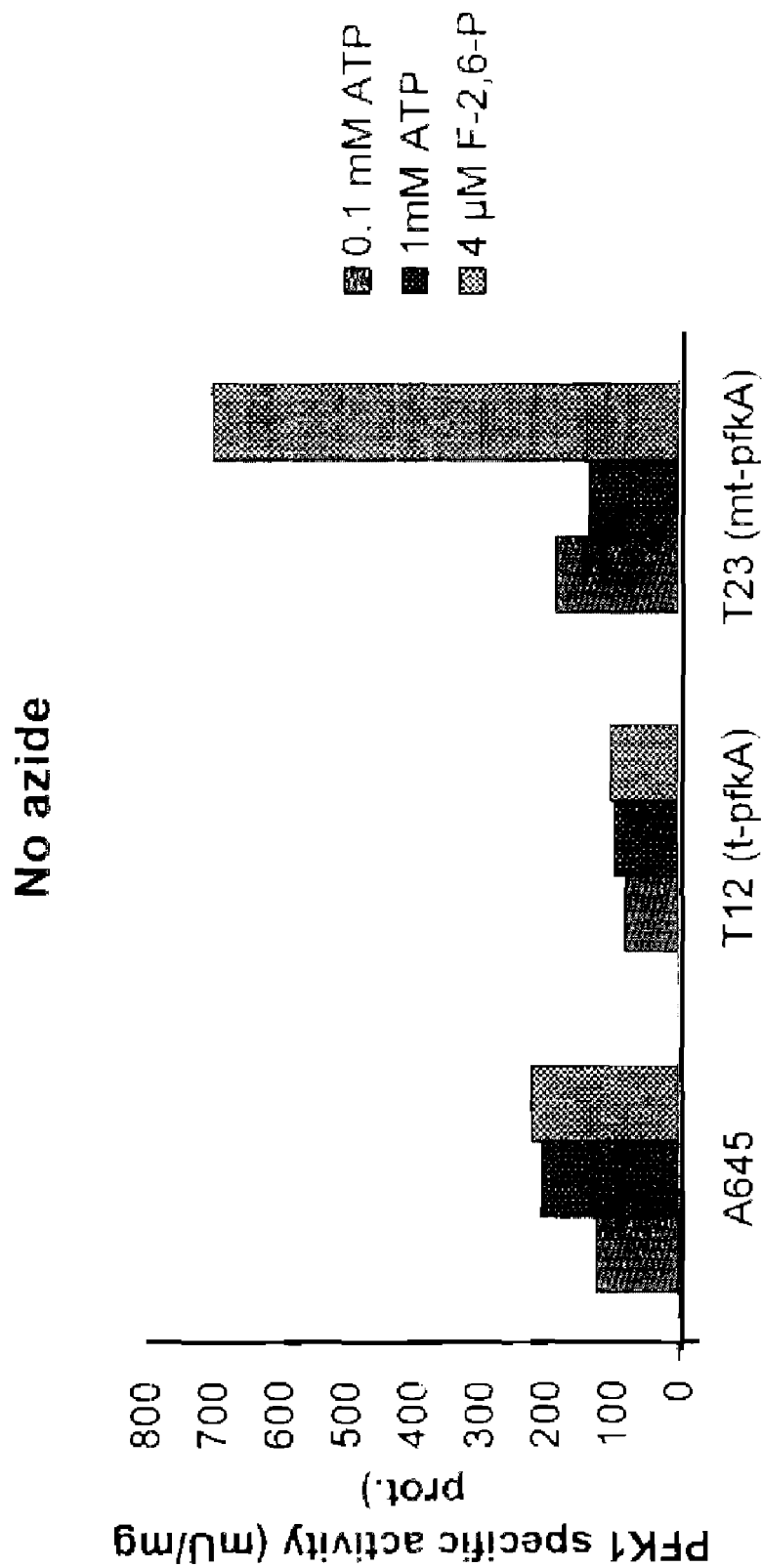
FIG. 2: Specific activities of PFK1 enzymes measured in homogenates of parental strain of *Aspergillus niger* (A645, which is a derivative of A158 strain), T12 transformant with integrated t-pfkA gene and An-TEGI-23 transformant with integrated mutated truncated mt-pfkA gene. No azide was added to the medium.

Abbreviation PFK1 stands for the enzyme 6-phosphofructo-1-kinase (EC 2.7.1.11).

Term "shorter fragment" stands for the protein which number of amino acid residues is smaller than that of the native protein.

Term "shorter PFK1 fragment" stands for the PFK1 protein which number of amino acid residues is smaller than that of the native 6-phosphofructo-1-kinase that is normally present in genetically unmodified cells.

Abbreviation "pfkA" stands for the gene encoding 6-phosphofructo-1-kinase.

Abbreviation "t-pfkA" stands for truncated pfkA gene, which number of nucleotides is lower than that of the native pfkA gene, encoding the synthesis of shorter PFK1 fragment, which number of amino acid residues is lower than that of the native PFK1 enzyme.

Term "mutation" stands for permanent change in nucleotide sequence of a specific gene.

Term "mutated pfkA gene" stands for a permanent change of one or more nucleotides anywhere in the sequence of pfkA gene encoding PFK1 enzyme with change of one or more amino acid residues anywhere in the protein.

Term "mutated mt-pfkA gene" stands for permanent change of one or more nucleotides anywhere in the sequence of truncated t-pfkA gene encoding shorter PFK1 fragment with change of one or more amino acid residues anywhere in the protein.

Term "6-phosphofructo-1-kinase" stands for the enzyme, that converts fructose-6-phosphate to fructose-1,6-bisphosphate on expense of ATP in the presence of $Mg^{2+}$ ions and is an enzyme in the process of glycolysis.

Term "inhibition by citric acid" stands for negative action of citric acid or its salts, such as citrates, on the enzyme activity of 6-phosphofructo-1-kinase.

Term "inhibition by ATP" stands for negative action of ATP on the enzyme activity of 6-phosphofructo-1-kinase.

Term "activation" stands for increasing the activity of the enzyme above the basic level in the presence of activating components such as: cellular metabolites, for instance fructose-2,6-bisphosphate and ammonium ions and AMP.

Term "N- and/or C-terminal part" of the protein stands for the part of the protein from the $NH_2$— group or beginning of the protein toward the central part of the protein and from the central part of the protein toward the COOH— group or the terminal part of the protein.

Term "post-translational modification" stands for a change in amino acid sequence of the protein by cleaving the protein by proteases or by attaching other bio-chemically functional groups to amino acid sequence, such as the addition of phosphate group by a process of phosphorylation catalysed by protein kinase. Post-translational modifications are described in the scientific literature.

Term "metabolites" stands for the products of cellular metabolism.

Term "anaplerotic reaction" stands for the process of replenishment of tricarboxylic acid cycle intermediates.

Term "originating or the native enzyme or the gene" stands for the enzyme of 6-phosphofructo-1-kinase and the gene encoding the enzyme, that is present in the cells of the wild type strain, which is the strain present in nature.

Term "recombinant origin" stands for the gene or protein that is modified by the laboratory techniques known to the experts from the field.

Term "synthetic origin" stands for the synthetically made gene or protein that is prepared by the techniques known to the experts from the field. Synthetic protein could be represented by the combination of animal and microbial protein.

Term "restriction at 5' and/or 3' part of the native gene" stands for the removal of the gene from 5' part toward the central part and/or removal from the central part toward the 3' part of the gene. Removal is conducted by techniques known to the experts from the field and can be done by specific endonucleases, unspecific cleavage or by multiplying the gene by the method of Polymerase Chain Reaction by the use of oligo-nucleotide primers, that are complementary to the gene at 5' and 3' end.

Term "mutated homologous recombinant gene" stands for the mutated gene encoding shorter fragment, prepared by the recombinant techniques and is introduced into the cells of the same species as the native gene comes from.

Term "mutated heterologous recombinant gene" stands for the mutated gene encoding shorter fragment, prepared by the recombinant techniques and is introduced into the cells of other species as the native gene comes from.

The invention deals with the gene encoding the shorter, genetically modified fragment of 6-phosphofructo-1-kinase that is active immediately after the synthesis, therefore no phosphorylation of protein molecule is needed for its activation; and in the presence of citric acid and/or citric acid salts up to concentration of 15 mM and ATP up to concentration 1.5 mM its activity is reduced for less than 30%; and can be activated by fructose-2,6-bisphosphate, ammonium ions and AMP; and is encoding a protein that differs for at least one amino acid residue of the original amino acid sequence of shorter fragments and which genes are present in the genomes of microbial, animal or plant origin, preferably fungi, preferably from the species *Aspergillus, Trichoderma, Penicillium, Pichia, Saccharomyces, Schizosaccharomyces, Candida, Kluyveromyces, Neurospora*, preferably *Aspergillus niger*. The gene encodes a shorter, genetically modified fragment of PFK1 with molecular mass higher than 30 kDa and lower than 55 kDa, which has no N- and/or C-terminal part of the native 6-phosphofructo-1-kinase.

The invention concentrates on the gene encoding the shorter, genetically modified fragment of PFK1 that is active immediately after the synthesis, therefore no phosphorylation of protein molecule is needed for its activation; and in the presence of citric acid and/or citric acid salts up to concentration of 15 mM and ATP up to concentration 1.5 mM its activity is reduced for less than 30%; and can be activated by fructose-2,6-bisphosphate, ammonium ions and AMP; and is encoding a protein with amino acid residue sequence SEQ ID NO: 1 or SEQ ID NO:2, that differs for at least one amino acid residue from amino acid sequence of the shorter PFK1 fragment of the sequence SEQ ID NO:3, which gene sequence SEQ ID NO:4 is present in the genome of *Aspergillus niger*; and encodes a protein with molecular mass higher than 30 kDa and lower than 55 kDa, which has no N- and/or C-terminal part of the native 6-phosphofructo-1-kinase.

The invention deals with an expression vector that carries the above mentioned gene functionally connected to controlling sequences, promoter, and other relevant DNA sequences enabling protein synthesis, which is coded by the gene and expression vector that enables expression of the gene in eukaryotic host cells or prokaryotic host cells, preferably animal tissue cultures, plant tissue cultures, filamentous fungi, yeasts, bacteria, preferably filamentous fungi, preferably from the genus *Aspergillus, Trichoderma, Penicillium*, and preferably yeasts, preferably from the genus *Pichia, Saccharomyces, Schizosaccharomyces*, and preferably bacteria, preferably from the genus *Acetobacter, Escherichia, Bacillus, Streptomyces, Zymomonas*, preferably in filamentous fungi of the genus *Aspergillus*, preferably *Aspergillus niger, Aspergillus terreus, Aspergillus oryzae*.

The invention deals with the organisms that contain above mentioned gene and/or above mentioned expression vector and that the above mentioned expression vector that corresponds to a specific organism, is inserted into above mentioned organism by the laboratory techniques known to the experts from the field in a way that enables expression of the above mentioned gene and the organisms are of microbial origin, preferably filamentous fungi, preferably from the genus *Aspergillus, Trichoderma, Penicillium*, and yeasts preferably from the gene *Pichia, Saccharomyces, Schizosaccharomyces*, or filamentous fungi from the genus *Aspergillus*, preferably *Aspergillus niger, Aspergillus terreus, Aspergillus oryzae*, or bacteria preferably from the genus *Acetobacter, Escherichia, Bacillus, Streptomyces, Zymomonas* and of plant and animal origin, preferably tissue cultures of plant and animal origin.

The invention concentrates on the use of the above mentioned gene and/or expression vectors and/or the above mentioned organisms for the rise of metabolic flux through glycolysis to enhance anaplerotic reaction during the process of bioproducts formation, preferably cell biomass; homologous and heterologous proteins; primary metabolites, such as ethanol, acetate, lactate, organic acids, amino acids, polyols; secondary metabolites, such as antibiotics, ergot alkaloids, statins, vitamins, immuno-modulators, citostatics, insecticides, herbicides.

The invention concentrates on the process for bio-products formation that include the use of the above mentioned gene that is inserted in the above mentioned expression vectors that is introduced into the above mentioned organisms and that the above mentioned organism is cultivated in a way to synthesise the bio-product.

The description of methods in the following text is merely of informative nature and serves for explanation of the invention. For the procedures other relevant materials and methods can be used known to the experts from the field.

1. DESIGNING AND TESTING MUTATED TRUNCATED GENE mt-pfkA

1.1.1. Growth of Fungus *Aspergillus niger*

Spores of the fungus *Aspergillus niger*, strain A60 (MZKI, Microbiological Collection of the National Institute of Chemistry, Ljubljana, Slovenia), that developed on the wort agar slant after 7 days of incubation at 30° C. were suspended in 25 ml of sterile Tween 80 solution (0.1%, w/v). Final concentration of spores was about $10^7$ spores per ml.

For rapid growth of biomass, complex medium was inoculated by spores that contained in 1 litre: 2 g glucose, 0.5 g yeast extract, 0.2 g casein acid hydrolysate, 6 g $NaNO_3$, 1.5 g $KH_2PO_4$, 0.5 g $MgSO_4 \times 7H_2O$, 0.5 g KCl, 10 ml trace metal solution (Vishniac and Santer, 1957), pH=6.0.

For enzyme kinetic determination the mycelium of parental strain and transformants was grown in the medium that contained in 1 litre: 20 g glucose, 5 g $NH_4(SO_4)_2$, 5 g $KH_2PO_4$, 1 g $MgSO_4 \times 7H_2O$, 0.5 g NaCl, 10 mg $MnCl_2$, 10 mg peptone, pH=6.0.

All media (100 ml) in 500 ml baffled Erlenmeyer flasks were inoculated by 5 ml of spore inoculum and incubated on a rotary shaker at 100 rpm and 30° C.

1.1.2. Preparing pyrG⁻ Auxotrophic Mutants

Single auxotrophic mutants of *Aspergillus niger* suitable for homologous transformation were prepared after the disruption of the pyrG gene in A158 strain (MZKI, Microbiological Collection of the National Institute of Chemistry, Ljubljana, Slovenia) by one step replacement method as described previously (Rothstein, 1983). Plasmid pGWII that was used for silencing of pryG gene, was prepared from pGW635 plasmid (Goosen et al., 1987) carrying pyrG gene of *A. niger* and pBluescript II KS+ (Stratagene, La Jolla, Calif.). From a 3.9 kbp long KpnI/XbaI digest of pGW635 a 0.8 kbp BglII/BamHI fragment of the pyrG gene was excised, while the remaining flanking regions (KpnI/BglII of 1.3 kbp and BamHI/XbaI of 1.8 kbp) were ligated and inserted into pBS vector. After transformation with pGWII plasmid, protoplasts were regenerated on the minimal medium in the presence of uridine (5 mM) and 5-fluoro-orotic acid (1 mg/ml). Recovered colonies were checked for auxotrophy. Auxotrophic pyrG⁻ mutant prepared from A158 strain was designated as A645.

1.1.3. Preparing pMOJ004 Plasmid

Expression vector pMOJ004 originates from pBluescript II KS+plasmid (Stratagene, La Jolla, Calif.) with integrated promoter region of gene encoding for glyceraldehyde-3-phosphate dehydrogenase (gpdA) and termination region of the gene encoding for glutamine amido transferase (trpC) of the fungus *Aspergillus nidulans*. Promoter gpdA (Z32524) was amplified by the PCR method by using pAN7-1 vector (Z32698) as a template and gpdA specific oligonucleotide primers: 5'-GAGCTCGTGACCGGTGACTCTTTC-3' (SEQ ID No: 5) and 5'-TCTAGATGCATATGGGTGATGTCT-GCTCAAGC-3' (SEQ ID No: 6), that simultaneously enabled the insertion of SstI and XbaI-NdeI restriction sites at the 5' end. Similarly trpC terminator region (X023390) was amplified by using the following oligonucleotide primers: 5'-CCATGGGTCTAGACGGATCCTAGTGATT-TAATAGCTCCATGTC-3' (SEQ ID No: 7) and 5'-GAAT-TCAAGCTTCCGCGGCCGGGTATTGGGTG-3' (SEQ ID No: 8) that simultaneously enabled the insertion of XbaI/BamHI and XhoI restriction sites at the 5' end. For preparing gpdA promoter PCR products were cut by SstI and XbaI enzymes, while for trpC terminator region the restriction was made by XbaI and XhoI enzyme. By using QIAquick GEL Extraction Kit (Qiagen) 0.9 and 1.5 kbp long fragments were isolated from the agarose gel. Finally PCR products were ligated into opened pBluescript II KS+ by the aid of T4DNA polymerase (New England Biolabs, Promega) and the newly formed plasmid was designated as pMOJ004 expression vector.

1.1.4. Construction of Truncated t-pfkA Gene

NdeI/ApaI-ATT-BamHI fragments of *A. niger* pfkA gene (EMBL Accession No. pfkA Z79690) was amplified by PCR reaction by using following primers: 5'-CCG CGG ATG CAT ATG GCT CCC CCC CAA GC-3' (SEQ ID No: 9) and 5'-TGG ATC CTC CTT ACC CGG GAT CAT AGT GCC GGC ACA GAC C-3' (SEQ ID No: 10) and subcloned into EcoRV digest of pBluescript II KS+ (pBS) (Stratagene, La Jolla, Calif.). After amplification of the pBS-t-pfkA plasmid in *E. coli* DH5α and the isolation of the plasmid by GeneElute Plasmid Mini Prep kit (Sigma), the t-pfkA sequence was determined by MWG-Biotech AG (Ebersberg, Germany) in positively oriented plasmids to exclude the appearance of any mutations. NdeI/BamHI digest of pBS-t-pfkA was finally ligated into pET3a plasmid for expression in bacteria and/or pMOJ004 for expression in filamentous fungi.

Truncated t-pfkA gene encoded a protein of 452 amino acids with molecular mass of 49.8 kDa. Protein has retained identical amino acid sequence of the N-terminal part of the native protein, however amino acid residues at position 451 and 452 were added to match the appropriate restriction site. After verifying the nucleotide sequence, the truncated t-pfkA gene was inserted into *Aspergillus niger* auxotrophic strain (pyrG−).

1.2.1. Introducing Site Directed Mutations into t-pfkA Gene

By studying three dimensional structure of PFK1 enzyme and by predicting phosphorylation sites of the amino acid residues of the enzyme using NetPhos 2.0 computer programme, the threonine residue at site 89 of the N-terminal part of the enzyme seemed to be the most likely candidate for phosphorylation and activation of the shorter PFK1 fragment. By site directed mutagenesis nucleotide triplets were changed on t-pfkA gene to substitute specific amino acid residues with analogous residues found on PFK1 enzyme of *E. coli*. Mutagenesis was conducted by QuikChange II XL Site-Directed Mutagenesis Kit (Stratagene, La Jolla, Calif.) by using the following oligonucleotide primers: for changing T89E, 5'-CC GCC CGC TGC ATG GAG TTC CGT GAG CGC CC-3' (SEQ ID No: 11) and 5'-GG GCG CTC ACG GAA CTC CAT GCA GCG GGC GG-3' (SEQ ID No: 12); for changing G95I, 5'-C CGC TGC ATG GAG TTC CGT GAG CGC CCC ATC CGT CTG CGG G-3' (SEQ ID No: 13) and 5'-C CCG CAG ACG GAT GGG GCG CTC ACG GAA CTC CAT GCA GCG G-3' (SEQ ID No: 14). After amplification of pET3a plasmid carrying mutated t-pfkA gene, the sequence of mutated t-pfkA gene has been verified (MWG-Biotech, Eberberg, Germany), in order to confirm the accuracy of the genetic change. Mutated t-pfkA gene was designated as mt-pfkA gene.

By using QuikChange II XL Site-Directed Mutagenesis Kit (Stratagene, La Jolla, Calif.) nucleotides of two codons were changed that enable replacement of two amino acid residues: threonine (T) at site 89 with glutamic acid (E) and glycin (G) at site 95 with isoleucine (I). After verifying the sequence of mutated truncated gene the construct was inserted into *A. niger* cells.

1.2.2. Insertion of Additional Mutations into mt-pfkA Gene. Construction of Mt-pfkA Gene Additional mutations were inserted into mt-pfkA gene encoding modified shorter PFK1 fragment of fungus *Aspergillus niger* to give a protein with 14 amino acid residues around the initial phosphorylation site of *A. niger* protein to be identical to *E. coli* protein. Nucleotide triplets for the synthesis of five more amino acid residues had to be changed as shown in Table 1.

TABLE 1

Additional changes introduced into genetically modified PFK1 fragment, encoded by Mt-pfkA gene.

| Amino acid residue in PFK1 protein of *A. niger* | Site at N-terminal part | Changed amino acid residue in a protein encoded by Mt-pfKA gene |
|---|---|---|
| Cysteine | 87 | Phenilalanine |
| Methionine | 88 | Proline |
| Glutaminic acid | 92 | Aspartic acid |
| Arginine | 93 | Glutamic acid |
| Proline | 94 | Asparagine |

Additional mutations in mt-pfkA gene were conducted by PCR method of two overlapping fragments with 297 and 1128 bases that formed 23 complementary bases. For amplification of both fragments, pMOJ004-mt-pfkA has been taken as a template. To enable insertion of MT-pfkA gene into pALTER-Ex1 plasmid (Promega), BamHI restriction site had to be replaced with XbaI restriction site at the 3' end of Mt-pfkA gene. Mt-pfkA gene was finally constructed by PCR ligation of both fragments. The oligonucleotide primers used are shown in Table 2.

TABLE 2

Oligonucleotide primers used for the construction of Mt-pfkA gene.

Amplification and mutagenesis of 297 bases long fragment

5'-CCATCGCACG<u>CATATG</u>GCTCC-3'
(SEQ ID No: 15)

5'-ATGTTCTCGTCACGGAACTCGGGGAAGCGGGCGGAACCGATCAAG-3'
(SEQ ID No: 16)

Amplification and mutagenesis of 1128 bases long fragment

5'-CCCGAGTTCCGTGACGAGAACATCCGTCTGCGGGCTGCC-3'
(SEQ ID No: 17)

5'-TAGGCGTTTATCGCTGCT<u>TCTAGA</u>GGATCCTTACCCGGGATCATAG-3'
(SEQ ID No: 18)

TABLE 2-continued

Oligonucleotide primers used for the construction of Mt-pfkA gene.

PCR ligation of both fragments

5'-CCATCGCACG<u>CATAT</u>GGCTCC-3'
(SEQ ID No: 19)

5'-TAGGCGTTTATCGCTGCT<u>TCTAGA</u>GGATCCTTACCCGGGATCATAG-3'
(SEQ ID No: 20)

Mt-pfkA gene was ligated into the pALTER-Ex1 plasmid under the control of tac promoter. After cloning the sequence of Mt-pfkA gene inserted into the pALTER-Ex1 vector was checked (MWG-Biotech, Edberg, Germany).

1.3.1. Transformation of *A. niger* Cells with pMOJ004-t-pfkA and pMOJ004-mt-pfkA Plasmid Mycelium of *A. niger* was harvested after 16-18 hours of submerged growth in a complex medium. Protoplast formation and transformation was conducted as reported previously (Kusters-van Someren et al., 1991), only that lytic enzyme Caylase-4 (Cayla, Toulouse, France) was used instead of Novozyme 234. As a selection marker pyrA gene located on pGW635 plasmid was used. Co-transformation of A645 auxotrophic strain was performed with 1 µg of pGW635 and 15 µg of pMOJ004-t-pfkA or pMOJ004-mt-pfkA carrying truncated or mutated truncated gene for the synthesis of modified shorter PFK1 fragment. Transformants were isolated after re-inoculation on medium without uridine.

1.3.1.1. Southern Analysis

Chromosomal DNA (3 µg) of transformants was degraded overnight by 30 U of BamHI restriction enzyme in a final volume of 200 µl. DNA molecules were separated on 0.5% agarose gel (1× Tris-acetate-EDTA buffer with 2 µl/ml of etidium bromide) and blotted on nylon membrane (Hybond™-N+, Amersham). Single stranded DNA was cross-linked to membrane by UV light (Biometra Ti3, Biometra, Goetingen, Germany). DNA probe was prepared from NdeI/BamHI cut of the pRCR-pfkA plasmid and labeled with BioPrime DNA Labeling System (Life Technologies) according to the instructions. Chemiluminescence detection with CDP-Star (Roche Applied Science) was done by exposure of membranes to X-Omat AR Film (Kodak).

Seventeen transformants with integrated truncated genes enabling the synthesis of the PFK1 fragment were isolated. Southern analysis showed different number of integrated plasmids in eleven transformants. Estimated number of integrated gene copies is presented in Table 3.

TABLE 3

Estimated number of truncated t-pfkA gene copies as detected after Southern analysis in total DNA isolated from various transformants.

| Strain | Parental strain (uridine auxotroph) | Plasmids taken for co-transformation | Estimated number of copies |
|---|---|---|---|
| ANPM 3 | A158 (A645) | pGW635, pMOJ004-t-pfkA | 10 |
| ANPM 4 | A158 (A645) | pGW635, pMOJ004-t-pfkA | 9 |
| ANPM 5 | A158 (A645) | pGW635, pMOJ004-t-pfkA | 6 |

TABLE 3-continued

Estimated number of truncated t-pfkA gene copies as detected after Southern analysis in total DNA isolated from various transformants.

| Strain | Parental strain (uridine auxotroph) | Plasmids taken for co-transformation | Estimated number of copies |
|---|---|---|---|
| ANPM 9 | A158 (A645) | pGW635, pMOJ004-t-pfkA | 12 |
| ANPM 14 | A158 (A645) | pGW635, pMOJ004-t-pfkA | 1 |
| ANPM 16 | A158 (A645) | pGW635, pMOJ004-t-pfkA | 1 |
| ANPM 29 | A158 (A645) | pGW635, pMOJ004-t-pfkA | 3 |
| ANPM 30 | A158 (A645) | pGW635, pMOJ004-t-pfkA | 5 |
| ANPM 31 | A158 (A645) | pGW635, pMOJ004-t-pfkA | 12 |
| ANPM 32 | A158 (A645) | pGW635, pMOJ004-t-pfkA | 10 |
| ANPM 34 | A158 (A645) | pGW635, pMOJ004-t-pfkA | 10 |

After co-transformation of mutated truncated mt-pfkA gene into the auxotrophic strain of *Aspergillus niger*, different numbers of integrated copies were detected by Southern analysis. Estimated numbers of copies are presented in Table 4.

TABLE 4

Estimated number of mutated truncated mt-pfkA gene copies as detected by Southern analysis in total DNA isolated from various transformants.

| Strain | Parental strain (Uridine auxotroph) | Plasmids taken for co-transformation | Estimated number of copies |
|---|---|---|---|
| An-TEGI1 | A158 (A645) | pGW635, pMOJ004-mt-pfkA | 1 |
| An-TEGI4 | A158 (A645) | pGW635, pMOJ004-mt-pfkA | 2 |
| An-TEGI5 | A158 (A645) | pGW635, pMOJ004-mt-pfkA | 2 |
| An-TEGI6 | A158 (A645) | pGW635, pMOJ004-mt-pfkA | 1 |
| An-TEGI12 | A158 (A645) | pGW635, pMOJ004-mt-pfkA | 1 |
| An-TEGI22 | A158 (A645) | pGW635, pMOJ004-mt-pfkA | 5 |
| An-TEGI23 | A158 (A645) | pGW635, pMOJ004-mt-pfkA | 5 |

1.3.2. Transformation of *Aspergillus terreus* with pMOJ004-mt-pfkA Plasmid

Mycelium of *A. terreus* was harvested after 16-18 hours of submerged growth in a complex medium. Protoplast formation and transformation was conducted as reported previously (Kusters-van Someren et al., 1991), only that lytic enzyme Caylase-4 (Cayla, Toulouse, France) was used instead of Novozyme 234. *A. terreus* transformants with integrated mt-pfkA genes were isolated after protoplasts were co-transformed with pMOJ004-mt-pfkA plasmid and pUT720 plasmid, carrying gene for phleomycin resistance.

1.3.2.1. Southern Analysis

In five strains the presence of mt-pfkA was confirmed by PCR method. Southern analysis revealed different number of integrated genes in individual transformants as presented in Table 5.

TABLE 5

Estimated number of mutated truncated mt-pfkA gene copies as detected by Southern analysis in total DNA isolated from various transformants of Aspergillus terreus.

| Strain | Parental strain | Plasmids taken for co-transformation | Estimated number of copies |
|---|---|---|---|
| At-TEGI1 | A156 | pUN720 pMOJ004-PFK10EI | 6 |
| At-TEGI2 | A156 | pUN720 pMOJ004-PFK10EI | 10 |
| At-TEGI3 | A156 | pUN720 pMOJ004-PFK10EI | 10 |
| At-TEGI4 | A156 | pUN720 pMOJ004-PFK10EI | 3 |
| At-TEGI5 | A156 | pUN720 pMOJ004-PFK10EI | 3 |

1.3.3. Transformation of Bacterium *E. coli* Strain DF 1010 with pALTER-Ex1 Plasmid Carrying Mt-pfkA Gene Plasmid pAlter-Ex1 carrying Mt-pfkA gene was inserted into *E. coli* strain DF 1010, with deleted bacterial pfkA and pfkB genes. Effectiveness of transformation was tested by growth of bacteria on selective medium. Plasmid pALTER-Ex1 contains a gene for expression of tetracycline resistance in bacterial cells.

1.4.1. Detecting the Activity of Shorter Fragment Synthesised from t-pfkA Gene Transformant with integrated t-pfkA gene were grown on minimal medium for 14 hours as described under 1.1.1. Sodium azide was added to the medium in final concentration of 1 mM and culture incubated for additional 15 minutes. Azide, a well known inhibitor of electron transport over cytochromes, causes protons to accumulate in the cells, which results in a drop of intracellular pH. Cells respond by the synthesis of a signalling molecule cyclic AMP to the slight acidification. Cyclic AMP activates cAMP-dependent protein kinase that ultimately phosphorylates shorter fragment of PFK1 encoded by t-pfkA gene. Different PFK1 kinetic parameters were detected in cell-free extracts of transformants after phosphorylation was induced, while no change in kinetics could be observed in parental strain in spite of induced phosphorylation.

1.4.2. Detecting the Activity of Shorter Fragment Encoded by mt-pfkA Gene.

Transformants with integrated mt-pfkA gene that enabled synthesis of modified shorter PFK1 fragment were grown for 14 hours on a minimal medium as described under 1.1.1. No sodium azide was added to the medium prior to measuring PFK1 kinetics in cell free extracts. The presence of active shorter fragment of PFK1 has been confirmed by detection of PFK1 kinetics characteristic for the shorter fragment.

1.5.1. Enzyme Tests 1.5.1.1 Homogenate Preparation

Mycelium was collected by suction filtration and washed with cold 50 mM phosphate buffer containing 0.5 mM dithio-erithritol (DTE) and 1 mM EDTA.

Approximately 50 g of wet weight of mycelium was frozen under the liquid nitrogen and disrupted for 1 minute in a glass bead disintegrator (Braun, Melsungen). After thawing the crushed cells were extracted with 5 ml of cold 50 mM phosphate buffer, pH=7,8, containing 0.5 mM DTE and 10 µl of protease inhibitor cocktail (Sigma). Finally the extract was centrifuged for 15 minutes at 15,000 rpm. Protein concentration in supernatant exceeded 5 mg/ml.

1.5.1.2. Measuring Enzyme Kinetics

PFK1 activity was measured spectrophotometrically at 340 nm according to slightly modified procedure of Legiša and Mattey, 1988, using a coupled reaction system. The reaction was carried out in the final volume of 1 ml and in the presence of: 50 mM Tris-HCl buffer, pH=7.8, 0.5 mM DTE, 200 mM KCl, 5 mM $MgCl_2$, 0.2 mM NADH, 20 µl of homogenate, various concentrations of fructose-6-phosphate, 0.9 U/ml aldolase (Roche Molecular Biochemicals, Indianapolis, Ind.), 2.4 U/ml triosephosphate isomerase and glycerol-3-phosphate dehydrogenase (Sigma), 4.5 U/ml aldolase (Sigma).

In order to remove ammonium ions the auxiliary enzymes were dialysed against 50 mM Tris-HCl buffer pH=7.8, 0.5 mM DTE, 30% glycerol, overnight at 4° C. with one change of buffer after 8 hours. The auxiliary enzymes remained active for several weeks when stored in refrigerator.

When kinetic parameters of the shorter fragment were determined, all measurements were conducted in a buffer containing 5 mg/ml of albumine, which was added to the system just before the measurements.

To differentiate between kinetics of the native enzyme and the shorter fragment, the measurements have started with adding fructose-6-phosphate and 0.1 mM ATP to the system, followed by increasing the concentration of ATP to 1 mM and finally in the presence of 4 µM of fructose-2,6-bisphosphate.

1.5.2. Demonstrating the Synthesis of the Shorter Fragment from t-pfkA Gene Since no active shorter fragment can be synthesised from t-pfkA gene, due to the need for phosphorylation of the protein molecule, intracellular phosphorylation must have been induced by an external stimulus. It has been achieved by adding sodium azide to the medium. Azide inhibits electron transport over cytochromes, which causes proton accumulation. Slight acidification is sensed as a stress in the cells that respond by the formation of signal molecule cAMP. Increased level of cAMP activates cAMP-dependent protein kinase that phosphorylates shorter PFK1 fragment, encoded by t-pfkA gene. In cell homogenates containing inactive shorter PFK1 fragment, changed enzyme kinetics was detected after induced phosphorylation (FIG. 1) that was characteristic for the shorter fragment. No alternation in enzyme kinetics could be observed in homogenate of parental strains, in spite of induced phosphorylation by azide. A series of other truncated pfkA genes were tested that coded for proteins shortened at C-terminal part, with molecular masses between 40 to 52 kDa and that differed for 8 amino acid residues. However, none of the other genes inserted into A. niger cells enabled synthesis of an active PFK1 enzyme with modified kinetics.

1.5.3. Demonstrating the Synthesis of Active Shorter PFK1 Fragment from mt-pfkA Gene For testing mt-pfkA gene intracellular phosphorylation was not induced by adding sodium azide to the medium before mycelium was homogenised and PFK1 activity measured. Parental strain, transformants with t-pfkA gene inserted and cells with mt-pfkA gene were tested for changed PFK1 activity. Enzyme kinetics characteristic for shorter PFK1 fragment were detected only in extracts from transformants carrying mt-pfkA gene, while normal PFK1 activity was observed in the parental strain and t-pfkA transformants.

1.5.4. Determining α-Amylolytic Activity in Filtrate

Alpha-amylolytic activity was measured in the medium filtrate as described under the Example 2.2., by using commercial Kit for evaluation of α-amylolytic activity according to the Ceralpha method (Megazyme, Bray, Ireland).

2. EXAMPLES

2.1. Testing *Aspergillus niger* Transformants for Increased Citric Acid Productivity For testing citric acid accumulation by *Aspergillus niger* strains the fungus was grown in a medium that contained the following ingredients in 1 litre: 150 g sucrose, 2.5 g $(NH_4)_2SO_4$, 1.5 g $KH_2PO_4$, 0.5 g $MgSO_4 \times 7H_2O$, 6.5 mg $FeSO_4$, 1.3 mg $ZnSO_4 \cdot 7H_2O$ with pH value adjusted to 2.5.

The amount of citric acid in the medium filtrate was determined as reported previously (Legiša and Jernejc, 2002). Data are means of five independent experiments inoculated with individual strain/transformant.

Figure 3:
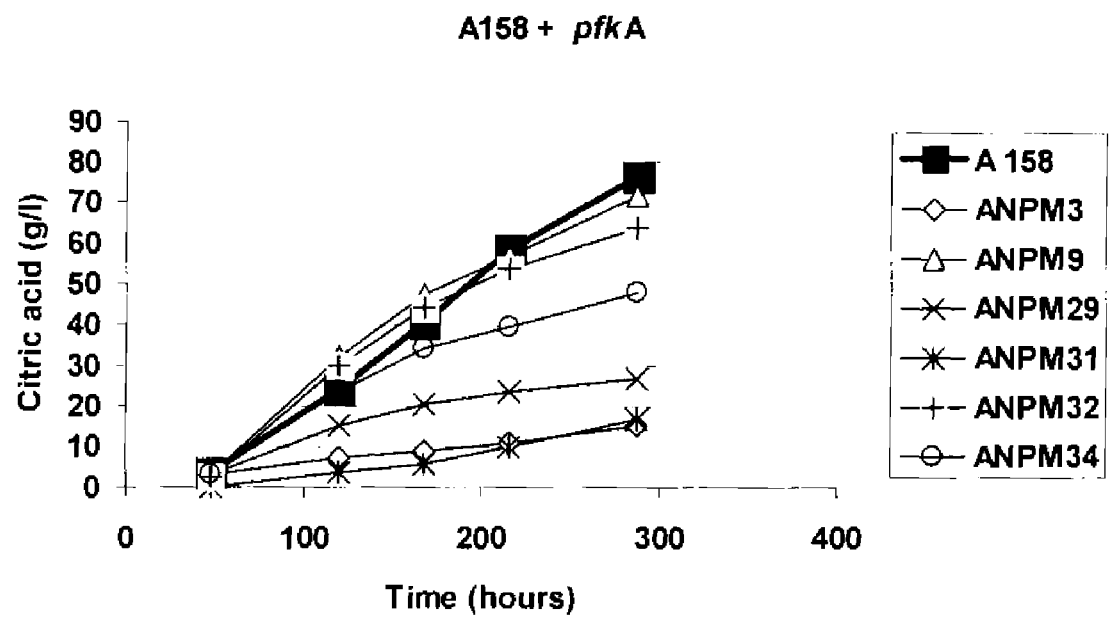
FIG. 3: Citric acid accumulation in the medium by *Aspergillus niger* strains transformed with truncated t-pfkA gene.
Figure 3:
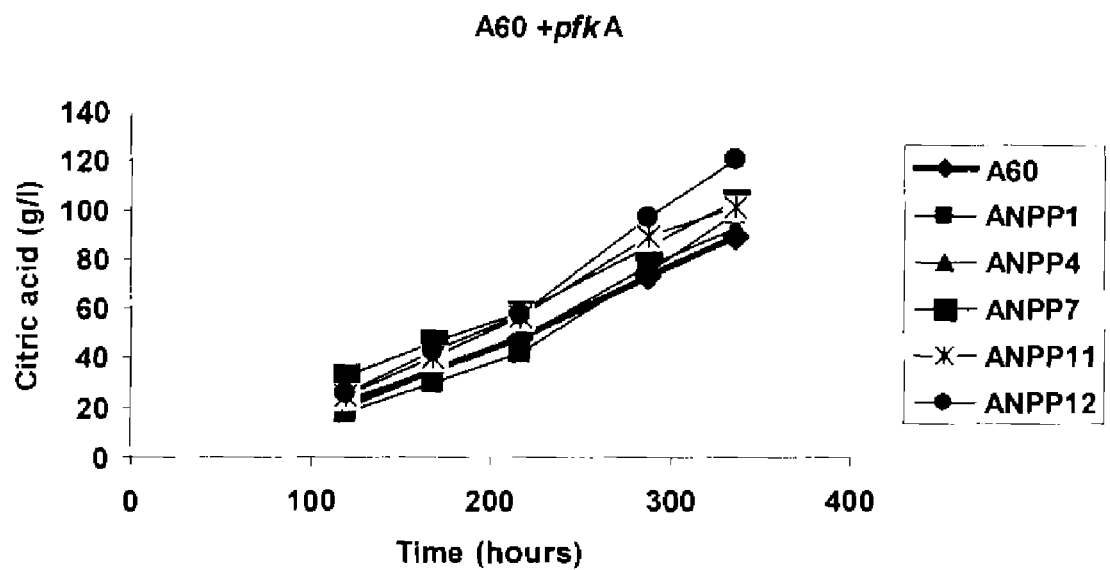

All transformants with inserted un-mutated truncated t-pfkA gene excreted citric acid more slowly and accumulated less acid in respect to the parental strain A158 (FIG. 3a). In *Aspergillus niger* strain A158 potent $H^+$-ATPases were described (Jernejc and Legiša, 2004) that can maintain pH homeostasis (Hesse et al., 2002). Lack of a slight intracellular acidification prevents triggering of cAMP synthesis and activation of cAMP-dependent protein kinase, therefore no phosphorylation and activation of inactive shorter PFK1 fragment can take place. In contrast to A158 strain, transformants of A60 strain with inserted t-pfkA gene showed increased citric acid production in respect to their parental strain (FIG. 3b). Less active $H^+$-ATPases were described in A60 strain (Jernejc and Legiša, 2002) that cause a drop of intracellular pH value during the growth in citric acid yielding medium, which finally induces cAMP synthesis and phosphorylation of the shorter PFK1 fragment.

Figure 4:
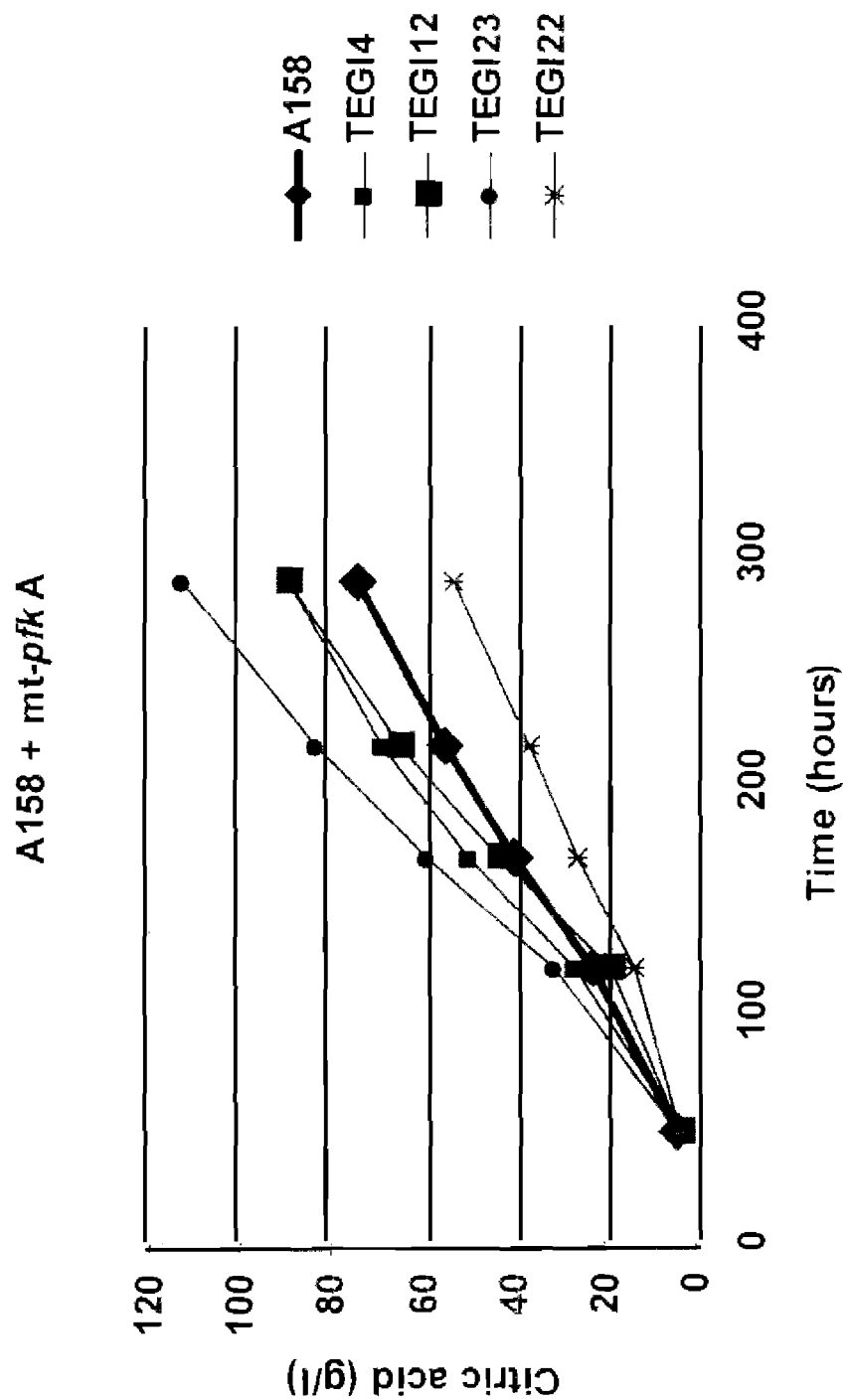
FIG. 4: Citric acid accumulation in the medium by *Aspergillus niger* transformants with integrated mutated truncated mt-pfkA gene. As a parental strain A645 strain, derivative of A158 strain has been taken.

On the other hand the majority of transformants with inserted mutated truncated mt-pfkA genes accumulated citric acid more efficiently in respect to A158 strain. With some strains more than 50% increased productivity was recorded, as well as product yields at the end of fermentation were increased, in comparison to the parental strain (FIG. 4). Some strains with inserted mt-pfkA genes indeed produced less citric acid, however it should be noted that during transformation plasmids might induce mutations during the insertion into the chromosome. In some transformants one plasmid copy might be inserted at a site that causes negative mutation in sense of good citric acid production.

Figure 5:
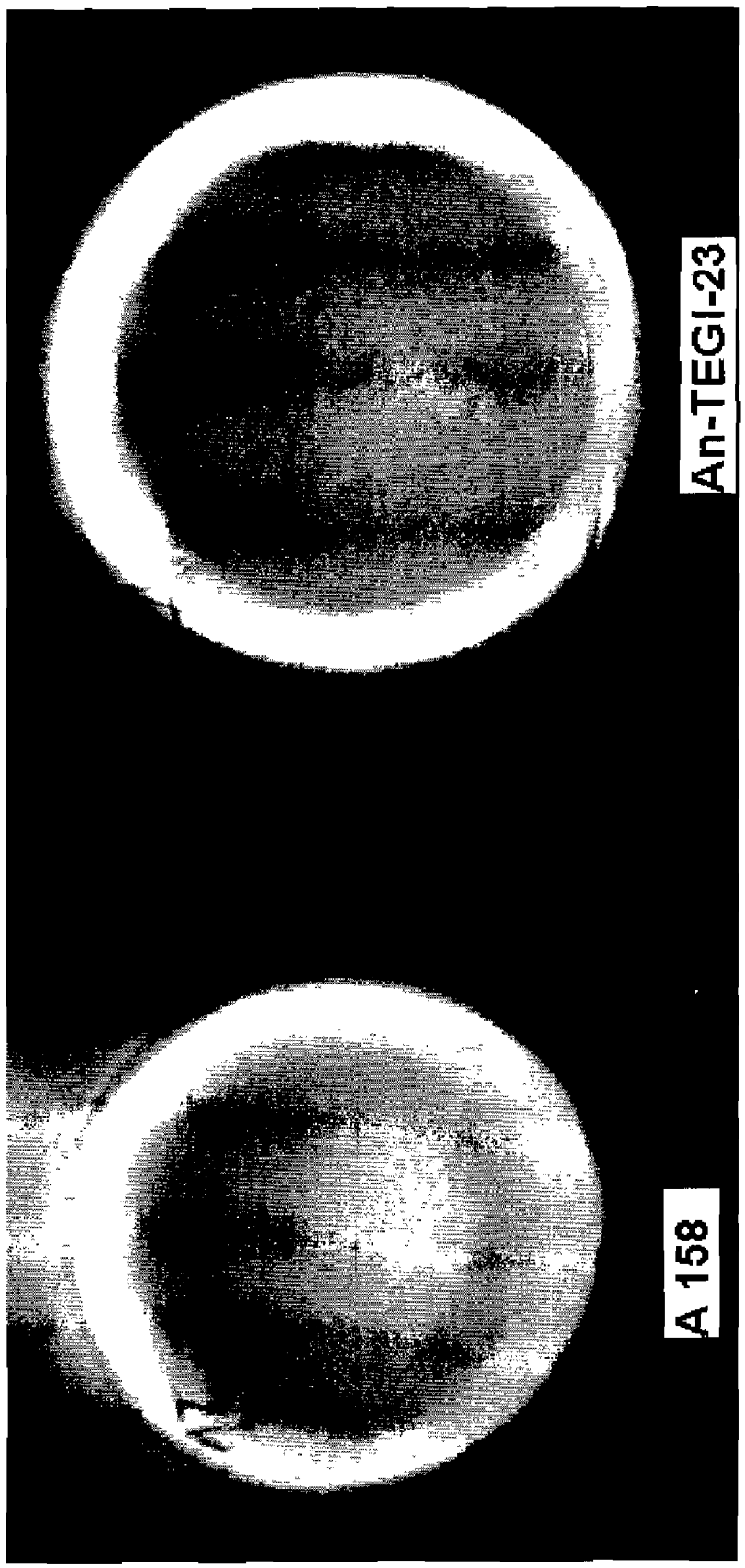
FIG. 5: Excretion of α-amylases by growing *A. niger* (A158 strain) and An-TEGI-23 transformant on the medium with starch as a sole carbon source. After three days of growth the remaining starch was stained by iodine solution. A clearing zone with no starch can be observed around the colony of An-TEGI-23. No clearing zone appeared around the colony of the parental strain.

2.2. Testing *Aspergillus niger* Transformants for Increased α-Amylase Productivity For testing α-amylase production the medium of the following composition was used that contained in 1 liter: 20 g starch, 6.0 g $NaNO_3$, 1.5 g $KH_2PO_4$, 0.5 g $MgSO_4 \cdot 7H_2O$, 0.5 g KCl, 0.1 g EDTA, 44 mg $ZnSO_4$, 10 mg $MnCl_2 \cdot 4H_2O$, 3.2 mg $CoCl_2 \cdot 6 H_2O$, 3.2 mg $CuSO_4 \cdot 5 H_2O$, 2.2 mg $(NH_4)_6Mo_7O_{24} \cdot 4 H_2O$, 14.7 mg $CaCl_2 \cdot 2H_2O$, 10 mg $FeSO_4 \cdot 7H_2O$, agar 1.5% (m/v). Agar plates containing the medium were inoculated with 5 μl of spore suspension of both *A. niger* strain A158 and transformant An-TEGI23. After three days of incubation at 30° C. the plates were poured with iodine solution ($J_2$ 0.4M/KJ 0.4M) and the clearing zones measured around the colonies (FIG. 5).

Transformant with integrated mt-pfkA genes grew faster and the colony diameter reached 26 mm, while the parental strain diameter was smaller—22 mm. After staining with the iodine solution a clearing zone could be observed around the colony of transformant, while no starch was degraded around the colony but only beneath the mycelium of the parental strain.

Figure 6:
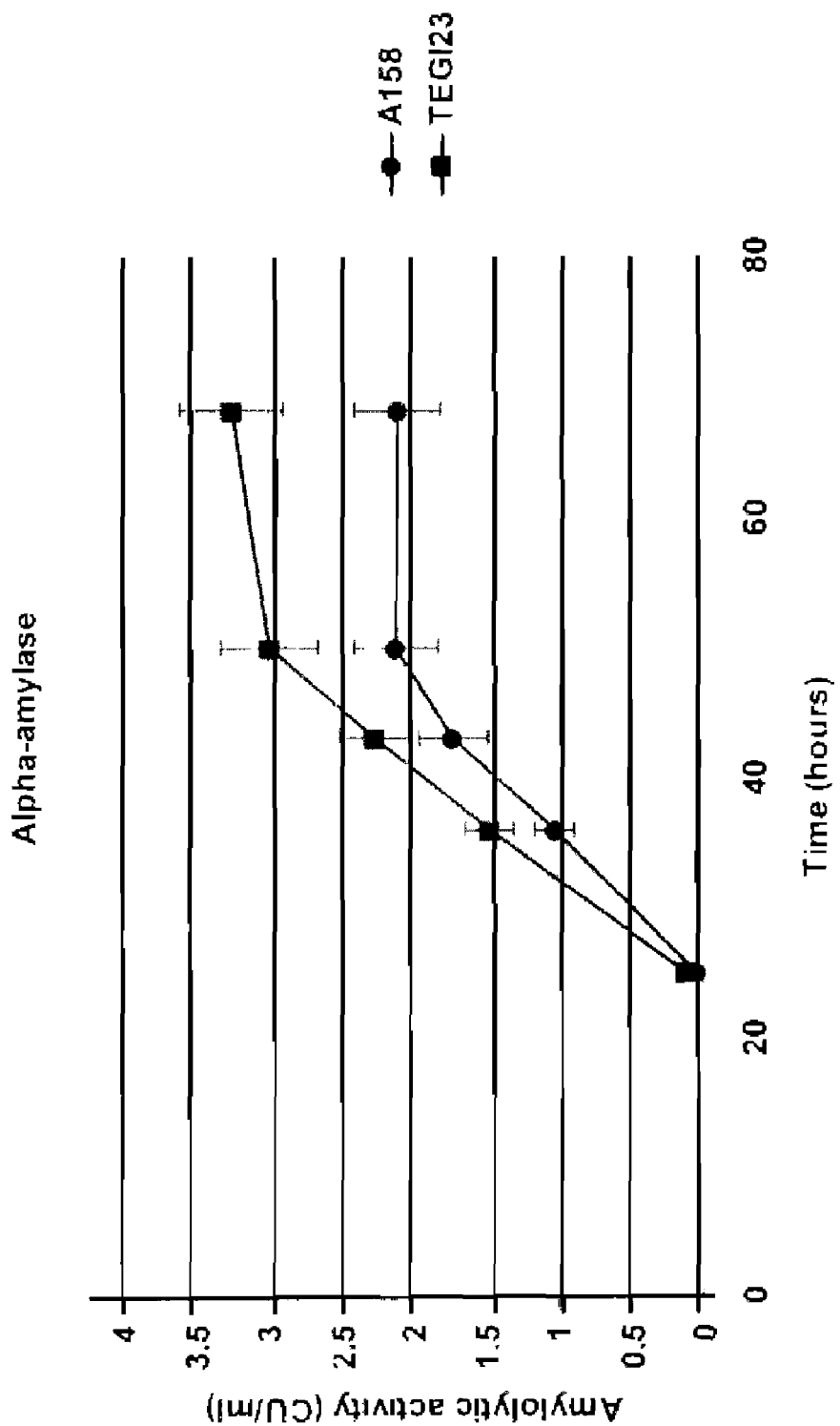
FIG. 6: Activities of extracellular α-amylases excreted by parental strain of *A. niger* (A158) and An-TEGI-23 transformant detected in the filtrate of the medium with starch as a sole carbon source.
Figure 7:
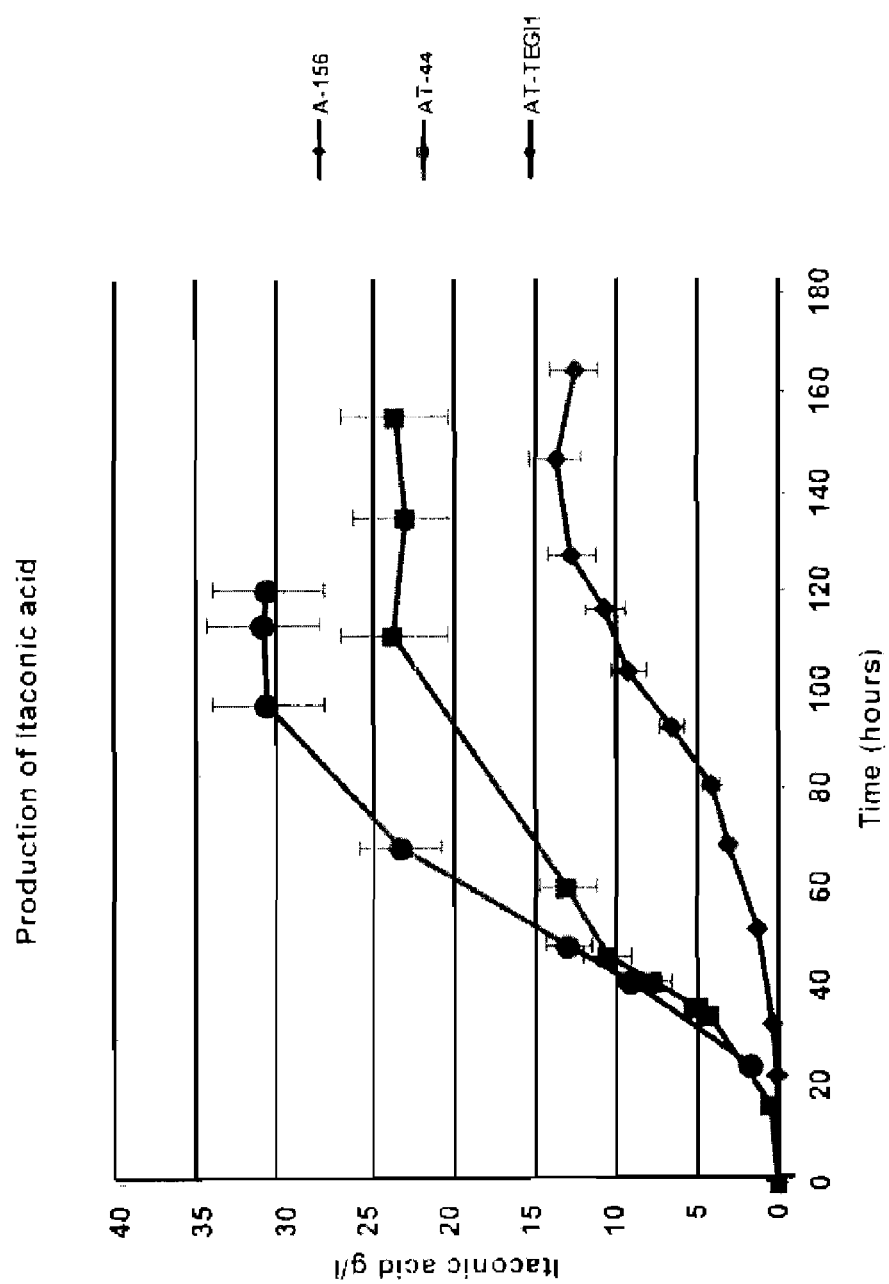
FIG. 7: Itaconic acid accumulation in the medium by transformants of *Aspergillus terreus* with integrated mutated truncated mt-pfkA gene (AT-TEGI1), integrated truncated t-pfkA gene (AT-44) and parental strain A156.

Alpha-amylolytic activity of the parental *A. niger* strain (A158) and transformant with integrated mt-pfkA genes (An-TEGI23) was detected during the submerged growth in the medium as described above, without agar added. The activity was determined in the filtrate of fermentation broths according to Ceralpha method. Data are means of three independent experiments and are shown in FIG. 6.

2.3. Testing *Aspergillus terreus* Transformants for Increased Itaconic Acid Productivity For testing itaconic acid excretion, the strains of *Aspergillus terreus* were grown in productive medium as described previously (Riscaldati et al., 2000) and contained in 1 litre: 150 g glucose, 2.36 g $(NH_4)_2SO_4$, 0.11 g $KH_2PO_4$, 208 mg $MgSO_4 \times 7H_2O$, 130 mg KCl, 74 mg NaCl, 0.2 mg $CuSO_4 \cdot 5H_2O$, 5.5 mg $FeSO_4 \cdot 7H_2O$, 0.7 mg $MnCl_2 \cdot 4H_2O$, 1.3 mg $ZnSO_4 \cdot 7H_2O$, pH adjusted to 3.4.

The amount of itaconic acid was determined by ionic chromatography by using CIM discs (Bia, Ljubljana, SI) and itaconate (Sigma) as a standard. The data are means of five independent experiments inoculated with the same strain/transformant. FIG. 6 shows the amount of accumulated itaconate by parental strain and transformant At-TEGI-1. In transformant carrying higher number of integrated mt-pfkA genes, the yields of itaconic acid were increased up to 40%.

2.4. Testing Transformants of Bacterium *E. coli* (DF 1020) for Growth on Specific Substrates Parental strains and double transformants of the bacterium *E. coli* were grown on minimal medium in the presence of the following carbon-hydrates as sole carbon sources: glucose, fructose, mannose and manitol. IPTG was added to the medium that promoted constitutive expression of Mt-pfkA gene. Apart from *E. coli* DE 1020 strain carrying Mt-pfkA gene the following *E. coli* strains were tested. BL21 strain, DF 1020 strain, DF 1020 strain with integrated native pfkA gene of *Aspergillus niger*, DF 1020 strain with integrated t-pfkA gene. After the incubation at 37° C. for several days, growth of individual colonies was observed. Growth rates of colonies have been evaluated and are shown in Table 6.

TABLE 6

Growth of *E. coli* transformants on the minimal medium with various carbon sources. More pulses indicate higher specific growth rate. Negative sign represents no growth.

| Sole carbon source | *E. coli* BL21 | *E. coli* DF1020 | *E. coli* DF1020 + n-n-pfkA | *E. coli* DF 1020 + Mt-pfkA |
|---|---|---|---|---|
| Glucose | ++ | + | ++ | ++ |
| Fructose | ++ | +++ | +++ | +++ |
| Mannose | ++ | − | ++ | +++ |
| Manitol | ++ | − | ++ | +++ |

REFERENCES

Arts, E. et al., Gen. Microbiol., 133 (1987), p. 1195-1199.
Capuder M., Bachelor Thesis. Ljubljana. University of Ljubljana Faculty for Chemistry and Chemical Technology, Studies of Biochemistry, (2004), 77.
Habison, A. et al., FEMS Microbiol. Lett. 5 (1979): 39-42.
Habison, A. et al., Biochem. J. 209 (1983): 669-676.
Hansen, T. et al., Arch. Microbiol. 177 (2002): 401-409.
Hesse S. J. A. et al., Eur. J. Biochem. 269 (2002): 3485-3494.
Huse. K. et al., FEBS Letts. 234 (1988): 185-188.
Jernejc, K./Legiša M., J. Biotechnol. 112 (2004): 289-297.
Kemp, R. G./Gunasekera, D., Biochem. 41 (2002): 9426-9430.
Kurland, I. J. et al., J. Biol. Chem. 267 (1992) 7: 4416-4423.
Kusters-van Someren, M. A., J. A. et al., Curr Genet. 20 (1991), 293-9.
Kurland, I. J./Pilkis, S., Protein Science 4 (1995): 1023-1037.
Legiša, M./Mattey M., Enzyme Microbiol. Technol. 10 (1988): 33-36.
Legiša, M./Benčina, M., FEMS Microbiol. Lett. 188 (1994a): 327-334.
Legiša, M./Benčina, M., FEMS Microbiol. Lett. 121 (1994b): 129.
Legiša, M./Kidrič, J., Appl. Microbiol. Biotechnol. 31 (1989): 453-457.
Laemmli. U. K., Nature 277 (1970): 680-685.
Li, Y. Et al., Biochem. 38 (1999): 16407-16412.
Mesojednik, S. Bachelor Thesis. Ljubljana. University of Ljubljana, Biotechnical Faculty, Department of Biology, (2003), 46.
Mesojednik, S./Legiša, M., Appl. Environment. Microbiol. 71 (2005): 3, 1425-1432.
Mlakar, T. Bachelor Thesis. Ljubljana. University of Ljubljana, Faculty for Chemistry and Chemical Technology, Studies of Biochemistry, (2003), 56.
Poorman, R. A. et al., Nature 309 (1984): 467-469.
Riscaldati, E. et al., J. Biotechnol. 83 (2000): 3, 219-230.
Ruijter, G. J. G. et al., Biochim. Biophys. Acta 1334 (1997): 317-326.
Schreferl, G. et al., J. Bacteriol. 165, 3 (1986), p. 1019-102.
Smerkolj, S. Bachelor Thesis. Ljubljana. University of Ljubljana, Biotechnical Faculty, Department of Microbiology, (2000), 32.
Valaitis, A. P. et al., J. Biol. Chem. 262, 11 (1987): 5044-5048.
Visniac, W./Santer, M. The Thiobacilli, Bacteriol Rev. 21 (1957), 195-213.
Voet, D./Voet, J. G. Biochemistry. Second edition. New York. Wiley & Sons inc., 1995, 1361.
Wang, X./Kemp, R. G. Biochemistry, 40 (2001): 3938-3942.

What is claimed is:

1. A nucleic acid sequence encoding a mutated and truncated 6-phosphofructo-1-kinase (PFK1) fragment of a wild type fungal PFK1 enzyme, wherein the nucleic acid includes at least one mutation selected from the group consisting of
    an encoded amino acid substitution at an amino acid that aligns with threonine 89 of SEQ ID NO: 3, and an encoded amino acid substitution at an amino acid that aligns with glycine 95 of SEQ ID NO: 3;
    wherein the mutation allows the PFK1 fragment to exhibit greater enzyme activity without phosphorylation than the wild type PFK1 without phosphorylation;
    wherein the truncated PFK1 fragment has less than 785 amino acids and is truncated at the C-terminus relative to the wild type PFK1; and
    wherein the PFK1 fragment has a molecular weight of about 30 kDa to about 55 kDa as determined by SDS-PAGE.

2. The nucleic acid of claim 1, wherein the PFK1 fragment loses less than 30% of its enzyme activity in the presence of citric acid and/or salts of citric acid in concentration up to 15 mM.

3. The nucleic acid of claim 1, wherein the PFK1 fragment loses less than 30% of its enzyme activity in the presence of ATP in concentration up to 1.5 mM.

4. The nucleic acid of claim 1, wherein the PFK1 fragment loses less than 30% of its enzyme activity in the presence of citric acid and/or salts of citric acid in concentration up to 15 mM and ATP in concentration up to 1.5 mM.

5. The nucleic acid of claim 1, wherein the substituted amino acid at an amino acid that aligns with amino acid 89 of SEQ ID NO: 3 is a glutamic acid.

6. The nucleic acid of claim 1, wherein the mutation includes the encoded amino acid substitution at an amino acid that aligns with amino acid 89 of SEQ ID NO: 3 and the encoded amino acid substitution at an amino acid that aligns with glycine 95 of SEQ ID NO: 3.

7. The nucleic acid of claim 1, wherein the substituted amino acid at an amino acid that aligns with amino acid 95 of SEQ ID NO: 3 is an isoleucine.

8. The nucleic acid of claim 1, wherein the truncated PFK1 fragment includes a mutation corresponding to a deletion of at least one amino acid from the N-terminus of the wild type PFK1.

9. The nucleic acid of claim 1, wherein the truncated PFK1 fragment includes a mutation corresponding to a deletion of at least two amino acids from the C-terminus of the wild type PFK1.

10. The nucleic acid of claim 1, wherein the PFK1 fragment includes a polypeptide comprising the amino acid sequence of SEQ ID NO: 1 or SEQ ID NO: 2.

11. The nucleic acid of claim 1, wherein the PFK1 fragment is from a genus of filamentous fungi.

12. A nucleic acid sequence that encodes a mutated and truncated PFK1 fragment of a wild type *Aspergillus* PFK1, wherein the truncated PFK1 fragment exhibits greater enzyme activity without phosphorylation than the wild type PFK1 without phosphorylation, wherein the nucleic acid sequence includes at least one mutation selected from the group consisting of an encoded amino acid substitution at an amino acid that aligns with threonine 89 of SEQ ID NO: 3, and an encoded amino acid substitution at an amino acid that aligns with glycine 95 of SEQ ID NO: 3, and wherein the truncated PFK1 fragment has less than 785 amino acids, has a molecular weight of about 30 kDa to about 55 kDa as determined by SDS-PAGE, and is truncated at the C-terminus relative to the wild type PFK1.

13. The nucleic acid of claim 12, wherein the PFK1 fragment loses less than 30% of enzyme activity in the presence of citric acid and/or salts of citric acid in concentration up to 15 mM.

14. The nucleic acid of claim 12, wherein the PFK1 fragment loses less than 30% of its enzyme activity in the presence of ATP in concentration up to 1.5 mM.

15. The nucleic acid of claim 12, wherein the PFK1 fragment loses less than 30% of its enzyme activity in the presence of citric acid and/or salts of citric acid in concentration up to 15 mM and ATP in concentration up to 1.5 mM.

16. The nucleic acid of claim 12, wherein the substituted amino acid that aligns with the amino acid 89 of SEQ ID NO: 3 is a glutamic acid.

17. The nucleic acid of claim 12, wherein the mutation includes the encoded amino acid substitution at an amino acid that aligns with amino acid 89 of SEQ ID NO: 3 and the encoded amino acid substitution at an amino acid that aligns with glycine 95 of SEQ ID NO: 3.

18. The nucleic acid of claim 12, wherein the substituted amino acid that aligns with the amino acid 95 of SEQ ID NO: 3 is an isoleucine.

19. An isolated nucleic acid comprising a sequence that encodes a polypeptide comprising the amino acid sequence of SEQ ID NO: 1 or SEQ ID NO: 2.

20. An isolated nucleic acid comprising a sequence that encodes the amino acid sequence of SEQ ID NO: 1 or SEQ ID NO: 2.

21. An isolated nucleic acid comprising a sequence that encodes a polypeptide comprising the amino acid sequence of SEQ ID NO: 1 with 0-6 amino acid substitutions, wherein the polypeptide exhibits greater enzyme activity without phosphorylation than the polypeptide of SEQ ID NO: 3 without phosphorylation.

22. A polypeptide comprising a mutated and truncated PFK1 fragment of a wild type fungal PFK1, wherein the PFK1 fragment exhibits greater enzyme activity without phosphorylation than the wild type PFK1 without phosphorylation; and wherein the truncated PFK1 fragment includes at least one mutation selected from the group consisting of an amino acid substitution at an amino acid that aligns with threonine 89 of SEQ ID NO: 3, and an amino acid substitution at an amino acid that aligns with glycine 95 of SEQ ID NO: 3, and wherein the PFK1 fragment has less than 785 amino acids, has a molecular weight of about 30 kDa to about 55 kDa as determined by SDS-PAGE, and is truncated at the C-terminus relative to the wild type PFK1.

23. The polypeptide of claim 22, wherein the PFK1 fragment loses less than 30% of enzyme activity in the presence of citric acid and/or salts of citric acid in concentration up to 15 mM.

24. The polypeptide of claim 22, wherein the PFK1 fragment loses less than 30% of enzyme activity in the presence of ATP in concentration up to 1.5 mM.

25. The polypeptide of claim 22, wherein the PFK1 fragment loses less than 30% of enzyme activity in the presence of citric acid and/or salts of citric acid in concentration up to 15 mM and ATP in concentration up to 1.5 mM.

26. The polypeptide of claim 22, wherein the substituted amino acid that aligns with amino acid 89 of SEQ ID NO: 3 is a glutamic acid.

27. The polypeptide of claim 22, wherein the substituted amino acid that aligns with amino acid 95 of SEQ ID NO: 3 is an isoleucine.

28. The polypeptide of claim 22, wherein the PFK1 fragment includes the amino acid substitution at an amino acid that aligns with amino acid 89 of SEQ ID NO: 3 and the amino acid substitution at an amino acid that aligns with amino acid 95 of SEQ ID NO: 3.

29. The polypeptide of claim 28, wherein the amino acid that aligns with amino acid 95 of SEQ ID NO: 3 is an isoleucine and the amino acid that aligns with amino acid 89 of SEQ ID NO: 3 is a glutamic acid.

30. The polypeptide of claim 22, wherein the PFK1 fragment includes a polypeptide comprising the amino acid sequence of SEQ ID NO: 1 or SEQ ID NO:2.

31. The polypeptide of claim 22, wherein the PFK1 fragment includes a polypeptide comprising the amino acid sequence of SEQ ID NO: 1 with 0 to 5 amino acid substitutions, deletions, and/or additions.

32. An isolated polypeptide comprising the amino acid sequence of SEQ ID NO: 1 or SEQ ID NO: 2.

33. A DNA including a first sequence which encodes a mutated and truncated PFK1 fragment of a wild type fungal PFK1, wherein the mutation allows the truncated PFK1 fragment to exhibit greater enzyme activity without phosphorylation than the wild type PFK1 without phosphorylation, and includes at least one mutation selected from the group consisting of an encoded amino acid substitution, addition, and/or deletion at an amino acid that aligns with threonine 89 of SEQ ID NO: 3, and an encoded amino acid substitution at an amino acid that aligns with glycine 95 of SEQ ID NO: 3, and
wherein the truncated PFK1 fragment has less than 785 amino acids, has a molecular weight of about 30 kDa to about 55 kDa as determined by SDS-PAGE, and is truncated at the C-terminus relative to the wild type PFK1; and wherein the first segment is fused in frame to a heterologous coding sequence.

34. An expression vector comprising a nucleic acid sequence encoding a mutated and truncated PFK1 fragment of a wild type fungal PFK1 origin having a molecular weight of about 30 kDa to about 55 kDa as determined by SDS-PAGE,
wherein the truncated PFK1 fragment exhibits greater enzyme activity without phosphorylation than the wild type PFK1 without phosphorylation,
wherein the truncated PFK1 fragment includes at least one mutation selected from the group consisting of an encoded amino acid substitution at an amino acid that aligns with threonine 89 of SEQ ID NO: 3, and an encoded amino acid substitution at an amino acid that aligns with glycine 95 of SEQ ID NO: 3; and
wherein the nucleic acid sequence is fused in frame to an expression control sequence.

35. A cultured cell comprising the vector of claim 34.
36. A filamentous fungi comprising the vector of claim 34.
37. A yeast comprising the vector of claim 34.
38. A bacteria comprising the vector of claim 34.
39. A method of producing bio-products, the method comprising:
obtaining an organism capable of producing bio-products;
inserting an expression vector into the organism, wherein the expression vector comprises a nucleic acid segment encoding a mutated and truncated PFK1 fragment of a wild type fungal PFK1,
wherein the truncated PFK1 fragment exhibits greater enzyme activity without phosphorylation than the wild type PFK1 without phosphorylation, and has a molecular weight of about 30 kDa to about 55 kDa as determined by SDS-PAGE,
wherein the nucleic acid segment is fused in frame to an expression control sequence,
wherein the nucleic acid segment includes at least one mutation selected from the group consisting of an encoded amino acid substitution at an amino acid that aligns with threonine 89 of SEQ ID NO: 3, and an encoded amino acid substitution at an amino acid that aligns with glycine 95 of SEQ ID NO: 3; and growing the organism.

40. The method of claim 39, wherein the expression vector enhances anaplerotic reaction during organism growth, thereby increasing bio-product production.
41. The method of claim 39, wherein bio-products are selected from cell biomass, homologous proteins, heterologous proteins, primary metabolites, and secondary metabolites.
42. The method of claim 39, wherein the nucleic acid segment is of filamentous fungal origin.
43. The method of claim 42, wherein the filamentous fungi is of a genera selected from the group consisting of *Aspergillus, Trichoderma*, and *Penicillium*.
44. The method of claim 39, wherein the organism is selected from the group consisting of a yeast, a filamentous fungi, and a bacterium.
45. The method of claim 44, wherein the yeast is of a genus selected from the group consisting of *Pichia* and *Saccharomyces*,
the filamentous fungi is of a genus selected from the group consisting of *Aspergillus, Trichoderma*, and *Penicillium*, and
the bacteria is of a genus selected from the group consisting of *Acetobacter, Escherichia, Bacillus, Streptomyces*, and *Zymomonas*.

* * * * *